(12) United States Patent
Cerisola et al.

(10) Patent No.: US 11,864,777 B2
(45) Date of Patent: Jan. 9, 2024

(54) ULTRASONIC SYSTEM

(71) Applicant: Mectron S.P.A., Genoa (IT)

(72) Inventors: Niccolò Cerisola, Genoa (IT); Andrea Cardoni, Madrid (ES)

(73) Assignee: Mectron S.P.A.

( * ) Notice: Subject to any disclaimer, the term of this patent is extended or adjusted under 35 U.S.C. 154(b) by 558 days.

(21) Appl. No.: 17/050,516

(22) PCT Filed: Apr. 26, 2019

(86) PCT No.: PCT/IB2019/053438
§ 371 (c)(1),
(2) Date: Oct. 26, 2020

(87) PCT Pub. No.: WO2019/207534
PCT Pub. Date: Oct. 31, 2019

(65) Prior Publication Data
US 2021/0219991 A1 Jul. 22, 2021

(30) Foreign Application Priority Data
Apr. 26, 2018 (IT) .......................... 102018000004895

(51) Int. Cl.
*A61B 17/16* (2006.01)
*A61B 17/32* (2006.01)
*A61C 1/07* (2006.01)

(52) U.S. Cl.
CPC ...... *A61B 17/1622* (2013.01); *A61B 17/1615* (2013.01); *A61B 17/320068* (2013.01); *A61C 1/07* (2013.01); *A61B 2017/320098* (2017.08)

(58) Field of Classification Search
CPC . A61B 17/16; A61B 17/1613; A61B 17/1624; A61B 17/1626; A61B 17/1628; A61B 17/1662; A61B 17/1673; A61B 17/32; A61B 17/320068; A61B 2017/320098; A61C 1/07; A61C 3/03
See application file for complete search history.

(56) References Cited

U.S. PATENT DOCUMENTS

| | | | |
|---|---|---|---|
| 10,893,883 B2 * | 1/2021 | Dannaher | A61B 17/320068 |
| 2009/0236938 A1 * | 9/2009 | Bromfield | B06B 1/0611 |
| | | | 310/323.19 |
| 2011/0278988 A1 | 11/2011 | Young et al. | |
| 2013/0253559 A1 | 9/2013 | Slipszenko et al. | |
| 2021/0219991 A1 * | 7/2021 | Cerisola | B06B 3/00 |
| 2022/0287798 A1 * | 9/2022 | Minutoli | A61C 17/16 |

(Continued)

FOREIGN PATENT DOCUMENTS

| | | | | |
|---|---|---|---|---|
| BR | 112020021887 A2 * | 1/2021 | ............. | A61B 17/16 |
| CN | 112236240 A * | 1/2021 | ............. | A61B 17/16 |
| CN | 112236240 B * | 5/2022 | ............. | A61B 17/16 |

(Continued)

*Primary Examiner* — Eric S Gibson
(74) *Attorney, Agent, or Firm* — Jason H. Foster; Kremblas & Foster

(57) ABSTRACT

An ultrasonic system includes generator means for ultrasonic microvibrations; waveguide means connected to and extending away from the generator means to bend at least in part; an operating element joined to a stationary bending node, so that flexural microvibrations are transmitted by the waveguide means to the operating element as alternating torsional or flexural microvibrations.

21 Claims, 16 Drawing Sheets

(56) References Cited

U.S. PATENT DOCUMENTS

2022/0313383 A1* 10/2022 Minutoli .......... G06K 19/07771

FOREIGN PATENT DOCUMENTS

| ES | 2913850 T3 * | 6/2022 | ............. A61B 17/16 |
|----|---|---|---|
| JP | H0373207 A | 3/1991 | |
| JP | 2021522045 A * | 8/2021 | ............. A61B 17/16 |
| KR | 20210016524 A * | 2/2021 | ............. A61B 17/16 |
| WO | WO-2019207534 A1 * | 10/2019 | ............. A61B 17/16 |
| WO | WO-2021028764 A1 * | 2/2021 | ............. A61B 90/98 |
| WO | WO-2021028790 A1 * | 2/2021 | ..... A61B 17/320068 |
| WO | WO-2021028792 A1 * | 2/2021 | ........... A61B 17/142 |

* cited by examiner

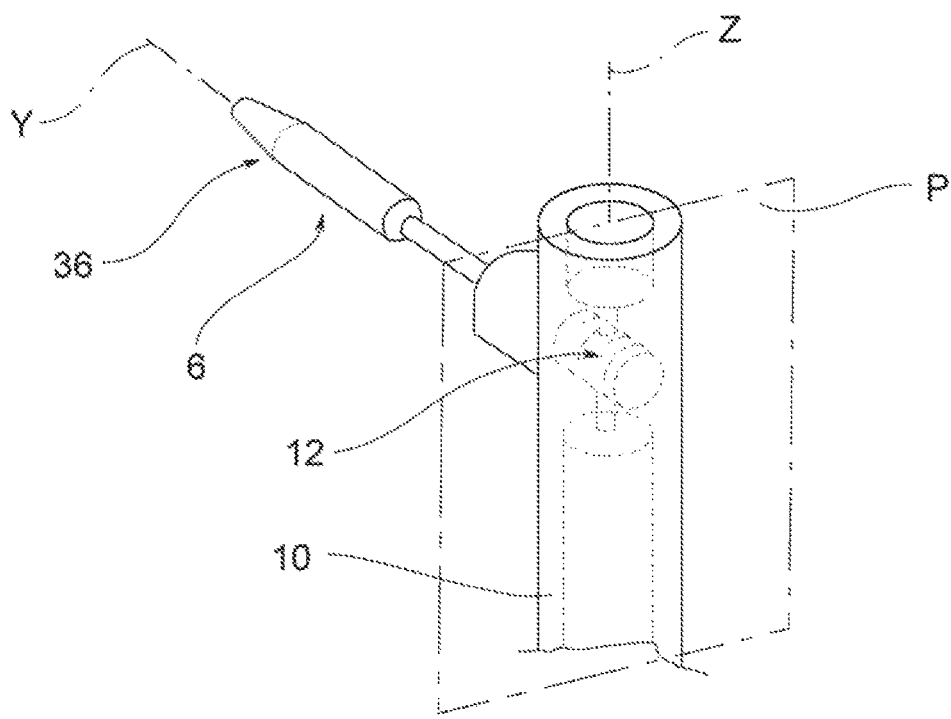
FIG.2a
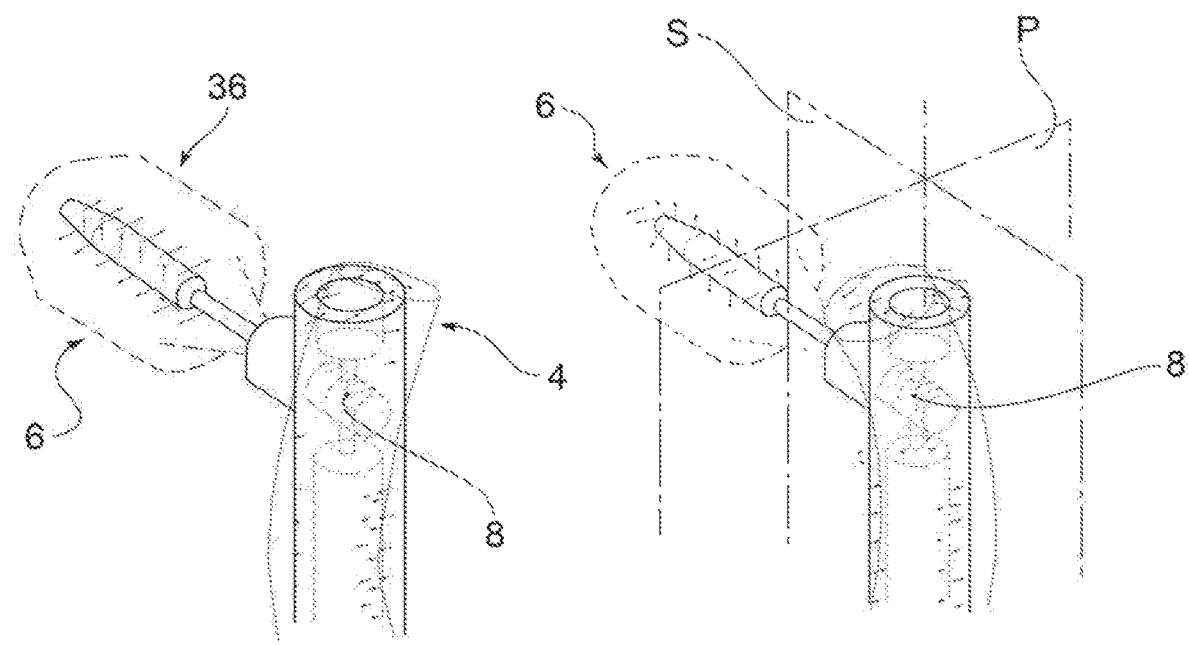
FIG.2b
FIG.2c

ULTRASONIC SYSTEM

CROSS-REFERENCE TO RELATED APPLICATIONS

This application is a National Phase Application of PCT International Application No. PCT/IB2019/053438, having an International Filing Date of Apr. 26, 2019 which claims the benefit of priority to Italian Patent Application No. 102018000004895, filed Apr. 26, 2018, each of which is hereby incorporated by reference in its entirety.

FIELD OF THE INVENTION

The present invention relates to an ultrasonic system, which finds a particular and advantageous application in the surgical field, in the dental field or in implantology, but which is likewise usable in the industrial or building field according to other embodiments.

More precisely, such a system can be used in sectors where it is necessary to carry out the removal or drilling of material, for example of the mineralized type, but not only of this type.

BACKGROUND OF THE INVENTION

According to the prior art, the making of holes or the removal of material is carried out by means of tools connected to spindles driven in rotation by possibly miniaturized motors (micromotors).

The main drawbacks of the known drilling or removal systems relate to: i) the generation of heat at the material on which one operates, since the friction to the tool and the heating of the (micro-) motor cause heating; ii) the ineffective removal of material debris which complicates the further removal of material in the form of debris; iii) the space available to the operator that could be sterically hindered.

Currently the ultrasonic vibrations generated piezoelectrically, or by magnetostriction, in solid, fluid, and multiphase media are applied in different fields of the industrial and medical sectors. Low intensity pressure waves produced at frequencies above 1 MHz are used to obtain information in relation to structures (industrial, civil and military) and internal organs of the human body (medical diagnosis). While high intensity waves at frequencies between 20 kHz and 100 kHz are excited in resonant devices to produce permanent changes in different application means. This last type of wave, commonly known as power ultrasound, is used in the manufacturing industry, for example to create interconnections in integrated circuits or weld thermoplastic materials, and in the food sector, for cutting sweets and other foods.

In the medical field, and specifically in the surgical field, power ultrasounds are applied in the dissection of hard tissues (bones) and soft tissues, in the cauterization of blood vessels, and in the dental field for the removal of tartar.

With reference to the field of implantology purely by way of example, the sites for inserting screws or other fixing systems into the bone are prepared by the use of rotating tools of the aforesaid type, which however have serious limitations, both at the intraoperative level for the operator, and postoperatively for the patient.

Only to mention a few, traditional instruments are problematic in the case of intervention on operating sites in the presence of complex anatomical structures of difficult or limited surgical access, or in the vicinity of delicate anatomical structures, such as nerves and blood vessels.

The large amount of mechanical energy produced by the rotation and the considerable pressure that the operator must apply to the instrument are responsible for possible damage to the non-mineralized structures, for the production of a considerable amount of heat, for losses due to friction, with a consequent overheating of mineralized tissues, fatigue of the operator to the detriment of precision and of the required intraoperative control.

The increase in intra-sital temperature is also caused by the possible insufficient removal of mineralized debris from the site of the intervention, the result of the drilling action, both at the level of the cutting elements of said instruments and at the level of the walls of the surgical site, with consequent formation of a layer of debris that obstructs the channels of the normal vascularization of the site, responsible for the osteo-regeneration process.

The present invention relates to ultrasonic power systems for use in the medical and dental field such as, for example, that of oral implantology to which we refer mainly to illustrate the advantages and inventive aspects of the proposed configurations. However, this invention is equally applicable in other fields of the medical and industrial sector.

The operation of most ultrasonic power systems is based on the transmission of longitudinal waves in the application means. These waves are generated by piezoelectric transducers and transferred in the media through concentrators or waveguides called ultrasonic horns.

However, there are applications where flexural, torsional or compound vibrations are used. In the dental field, for example, the longitudinal vibrations excited in the ultrasonic transducers are converted into flexural oscillations through the coupling to asymmetrically shaped inserts or bits. The incorporation of one or more curves in the insert profile has a double objective: to allow good access to the inside of the oral cavity, and to convert the longitudinal movement of the transducer into a linear flexion vibration close to the operative part of the insert.

In ultrasonic scalers, the bending movement of hooked inserts is normally used to remove calcified deposits (tartar) from the teeth. In ultrasonic scalpels (such as the "Piezosurgery device" by Mectron spa), the transverse movement produced in sickle-shaped inserts is used to precisely dissect the mandibular bones and other mineralized tissues.

There are also ultrasonic scalers that remove tartar through both linear and elliptical oscillations, as described for example in DE102005044074A1 or in EP2057960B1. In these systems, vibratory movements having bidirectional components are generated in the inserts by flexural vibrations of the transducer on orthogonal planes, see in particular EP2057960B1. The configurations of these bending transducers are based on a previously disclosed concept in which the transverse oscillation is caused by adjacent piezoelectric volumes inserted radially and axially with opposite polarizations [see Mori, E. et al., "*New Bolt Clamped Flexural Mode Ultrasonic High Power Transducer with One-Dimensional Construction*", Ultrasonics International 89 Conference Proceedings"; Watanabe, Y. et al., "*A Study on a New Flexural-mode Transducer-solid Horn System and its Application to Ultrasonic Plastic Welding*", Ultrasonics Vol. 34, 1996, pp. 235-238; Yun, C-H. et al. "*A High Power Ultrasonic Linear Motor using a Longitudinal and Bending Hybrid Bolt-Clamped Langevin Type Transducer*", Jpn. J. Appl. Phys., Vol. 40, 2001, pp. 3773-3776].

In maxillofacial surgery procedures, the ultrasonic oscillations of the inserts are commonly used to cut the bone tissue. To date, there is no ultrasound device capable of piercing the jaw with the same efficiency with which the latter can be cut. For this reason, applications such as the preparation of the implant site are still performed almost exclusively using cutters driven by micromotors.

According to the dental implant protocol, once a first hole of reduced dimensions is made, it is progressively widened using rotating burs with a growing section until it reaches a diameter compatible with the implant.

Inserts typically used in ultrasound systems for operations performed in the oral cavity have insufficient oscillatory amplitudes to perform all stages of implant site preparation. This limitation is inherent in the design of these devices in which, for the same handpiece, the greater the cross sections of the inserts, the smaller the amplitudes of vibrations produced are. This inverse relationship between the section and the oscillation of the inserts represents a limit of applicability of the technology, especially in oral implantology where it is necessary to obtain holes of several millimeters in diameter.

There is a further problem linked to the linear vibration of the inserts which does not allow the piercing of the mandibular tissue unless there is the application, combined therewith, of a manual tilting of the handpiece. This auxiliary movement is certainly difficult to produce by the operator inside the mouth and is in any case not very compatible with the precision requirements that implantology practice today requires.

Ultrasound devices capable of dissecting biological tissues by excitation of ultrasonic torsional, or combined torsional and longitudinal vibrations, are known from U.S. Pat. No. 7,374,552B2, U.S. Pat. No. 6,402,769B1, US2009/236938A1, US2011/0278988A1. The common feature of these devices is that they all have a single geometric development axis, being essentially axial-symmetrical systems. In maxillofacial applications, such as dental implantology, the oscillating inserts used in the oral cavity have remarkably asymmetric developments with respect to the transducer axis. Therefore in these areas it is not possible to produce torsional or longitudinal and torsional vibrations in the operative parts of the inserts following the dictates of the mentioned inventions (valid only for systems in which transducers and operating parts are coaxial).

Slipszenko (US2013/0253559A1) has devised configurations of ultrasonic systems in which torsional, flexural or longitudinal vibrations are alternatively produced in ultrasonic scalpels for the treatment of soft tissues with a development axis perpendicular to that of the transducer. According to this solution, the transverse vibration of the piezoelectric transducer can be transformed into torsional, flexural or longitudinal oscillation by incorporating an ultrasonic or waveguide horn mounted eccentrically with respect to the transducer axis. In order for the vibration transmission to take place correctly, the diameter of the rear part of the horn must be greater than that of the transducer. Although it is possible to generate alternating vibratory families on orthogonal planes, the requirements of compactness, ergonomicity and specific weight of dental and maxillofacial devices cannot be achieved by applying Slipszenko's solution. The high dimensions and the eccentric mounting of the ultrasonic horn would considerably limit the visibility inside the oral cavity. Furthermore, in the Slipszenko solution one or more waveguides are inserted between the scalpel and the vibratory transmission/conversion horn to transmit adequate vibrations. Even reducing the number of these components to a minimum, the overall length of the device would still be incompatible for applications inside the oral cavity.

Mishiro (JPH0373207A) proposed an ultrasonic system for the removal of material that could theoretically find applicability in dental applications. The proposed solution is based on a principle of operation typical of ultrasonic motors in which the elliptical vibration generated in a joint formed by an ultrasonic transducer coupled to a waveguide produces the rotation of an operating element (tool) kept in contact with the waveguide tip. In the configurations shown in JPH0373207A, the operating element, whose symmetry axis can be perpendicular or parallel to that of the transducer, in addition to rotating oscillates ultrasonically, thus allowing the removal of material. The point of contact between the operating element and the waveguide through which the oscillatory movement is transferred is generated by the rotation corresponds with an antinode of the longitudinal and transverse vibrations generated in the transducer-waveguide joint. According to the configurations described in this solution, the operating element is supported by two bearings positioned at the same number of stationary nodes produced along the oscillating element. This solution appears complex in its construction and unsuitable for applications in which the operative elements (inserts) are to be used and replaced in succession as in dental implantology.

SUMMARY OF THE INVENTION

The present invention proposes alternative configurations of the transducer/insert joint which allow producing flexural, torsional, or combined longitudinal and torsional vibrations of adequate amplitudes for the preparation of the implant site and the execution of other applications.

The invention relates to the introduction of new configurations of transducer/insert systems suitable for performing operations within the oral cavity. By means of the solutions described below it is possible to generate flexural, torsional, or combined torsional and longitudinal ultrasonic oscillations in the operative part of the inserts at sufficiently high amplitudes for the preparation of the implant site. The development axes of the inserts and of the coupled flexural transducer can be incident, orthogonal and coplanar.

In particular, the combined flexural, or torsional and longitudinal vibrations can be used to make the first hole of the implant procedure; while the torsional or torsional and longitudinal oscillations generated in appropriately configured inserts allow the subsequent steps to widen the initial hole to be carried out.

In each configuration described and illustrated below, the coupling between the inserts and the transducer takes place through a bending node.

Some of the main advantages that derive from this invention are:
  i) the achievement of high vibrations of the operating parts of the inserts useful for conducting operations in limited access spaces;
  ii) reduced dimensions (small inserts);
  iii) greater versatility regarding the design of the inserts;
  iv) modal parameters and electro-mechanical efficiency of the transducer almost unchanged despite the coupling with different inserts;
  v) possibility of carrying out the implant site preparation using a single transducer in conjunction with a set of inserts with specific geometric and oscillatory features.

The present invention therefore provides a universal solution applicable both in maxillofacial surgery and in other sectors in the medical and industrial fields.

The present invention falls within in the above context, proposing to provide an ultrasonic system which works according to dynamics different from the traditional rotation in a single direction, and which by virtue of the innovative alternating motion described allows obtaining advantageous results in relation to a reduced overheating, advantageous with regard to the better removal of debris from the site of use, advantageous in relation to reduced overall dimensions.

This object is achieved by an ultrasonic system as described and claimed herein. Preferred or advantageous embodiments are also described.

BRIEF DESCRIPTION OF THE DRAWINGS

The object of the present invention will now be described in detail, with the aid of the accompanying drawings, in which:

FIGS. 2A, 2B, 2C show enlargements of the distal area, that is to say, at the operating element of the ultrasonic system shown respectively in FIGS. 1A, 1B, whereas FIGS. 2B, 2C illustrate two successive operating instants in a vibratory resonance cycle, these instants being in particular out of phase by about 180°;

FIGS. 22, 23, 24 illustrate a perspective view of an ultrasonic system, object of the present invention, according to another possible variant, and two enlargements of the distal area, that is to say, at the operating element of the ultrasonic system shown in FIG. 22, whereas FIGS. 23, 24 illustrate two successive operating instants in a resonance vibratory cycle, these instants being in particular out of phase by about 180°, along mutually different axes;

DETAILED DESCRIPTION

Figure 1A:
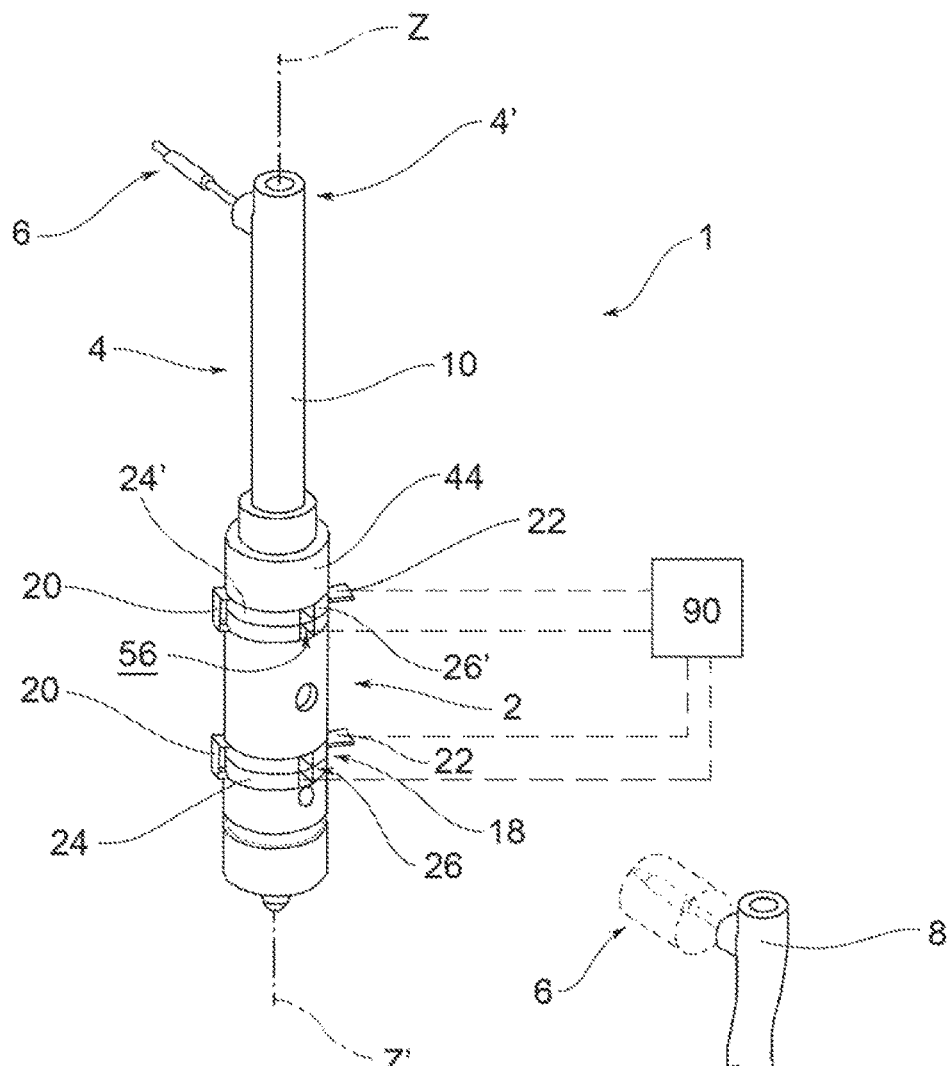
FIGS. 1A, 1B show perspective views of an ultrasonic system according to the present invention, according to a first possible embodiment, in a non-operating configuration and in an operating (or resonant) configuration, respectively, the latter calculated by means of a finite element analysis.

In the above drawings, reference numeral 1 indicates as a whole an ultrasonic system 1 comprising ultrasonic microvibration generator means 2, waveguide means 4 connected to the generator means 2 and at least one operating element 6.

The term "waveguide" means a body or portion of a body which, thanks to its geometry and location, that is to say, also to the connection thereof to said generator means 2, concentrates and/or amplifies a flexural vibration of the generator means 2. Such a component or portion of the ultrasonic system 1 is also called "concentrator" because it concentrates (and preferably but not necessarily amplifies) the flexural vibration of the generator means 2, for example through the reduction of the cross section thereof in at least one distal portion thereof. This component or portion of the ultrasonic system 1 is also called ultrasonic horn.

According to an embodiment, said waveguide 4 is in axis with or coaxial to said generator means 2.

According to an embodiment, said generator means 2 comprise a plurality of piezoelectric elements 18 spaced apart from each other by a mass body 42 and associated proximally with a mass body 40 or tuner and distally with a further mass body 44. These mass bodies 40, 42 and 44 allow with their predefined mass to calibrate the operating frequency or frequencies of the generator means 2.

For example, this ultrasonic system 1 is a surgical instrument, for example a bone drill, or a dental instrument. According to other embodiments, the present system 1 is an industrial instrument or can be used in the construction field, such as for example a milling cutter, a drill, or a cutting tool.

According to different embodiments, the operating element 6 comprises a drilling bit 34, a material removal cutter 36, a (semi-)spherical element, a reamer member or a cutting member (variants not shown).

According to an embodiment (for example see the variant in FIG. 10), the generator means 2 comprise at least one longitudinal ultrasonic transducer 74 (as defined hereinafter), in particular of the Langevin® type.

According to an embodiment, the generator means 2 comprise at least one ultrasonic transducer 16, 74 comprising one or more piezoelectric elements 18 placed in electrical contact with at least one pair of contact electrodes 20, 22.

According to an embodiment, the ultrasonic transducer 16, for example also of the Langevin type, is of the bending type.

According to an embodiment, the ultrasonic transducer 16, 74 comprises a plurality of piezoelectric elements 18 placed side by side, for example along an assembly direction Z'.

According to an embodiment, the ultrasonic transducer 16, 74 is arranged or mounted coaxially to a prevailing development direction Z of the waveguide means 4.

It should be noted that in this description, the expressions "axial", "radial", "transverse", "longitudinal" always refer to the prevailing development direction Z, unless otherwise specified.

According to an embodiment, the aforementioned assembly direction Z' is substantially parallel to, or coincident with, the prevailing development direction Z.

According to one embodiment, at least one piezoelectric element 18 is arranged at an antinode 58 of the flexural microvibration, in particular in an ultrasonic transducer 16 of the flexural type.

According to an embodiment, the ultrasonic transducer 16 comprises at least one pair of mass bodies 40, 42, 44, which axially enclose at least one piezoelectric element 18.

According to an embodiment, one or more mass bodies 40, 42, 44 (for example: all) are made of metallic material.

According to an embodiment, the piezoelectric element 18, the contact electrodes 20, 22 and the optional mass bodies 40, 42, 44 are independently of an annular or tubular shape, and are mounted mutually coaxially with respect to the assembly direction Z'.

According to an embodiment, the piezoelectric element 18, the contact electrodes 20, 22 and the optional mass bodies 40, 42, 44 may have a cross section—with respect to the prevailing development direction Z or with respect to the assembly axis Z'— that is circular or polygonal (for example square or rectangular).

According to an embodiment, the piezoelectric element 18, the contact electrodes 20, 22 and the optional mass bodies 40, 42, 44 are mounted on a connecting stem 46 (or captive stem) which passes therethrough axially (specifically: with respect to the assembly direction Z').

According to an embodiment, the mass bodies 40, 42, 44 of the ultrasonic transducer 16 provide axial compression elements of the piezoelectric element 18 and of the contact electrodes 20, 22, or of the plurality of piezoelectric elements 18 and of contact electrodes 20, 22.

According to an embodiment, the mass bodies 40, 44 of the ultrasonic transducer 16, 74 arranged in an axial end position may comprise first threads 48, 50 configured to couple with second threads 52, 54 delimited by the connecting stem 46, for example one in an end position and one in an intermediate or central position thereof.

According to an embodiment, one or more piezoelectric elements 18 of the ultrasonic transducer 16 comprise a pair of half-elements 24, 26 (or parts of element 24, 26) with mutually opposite polarization directions and side by side in an oscillation plane P. In this way, upon the application of an alternating electrical voltage to the contact electrodes 20, 22, alternatively a half-element (24 or 26) expands while the other half-element (26 or 24) of the pair contracts to generate the flexural microvibrations in the generator means 2 and in the waveguide means 4.

Figure 4:
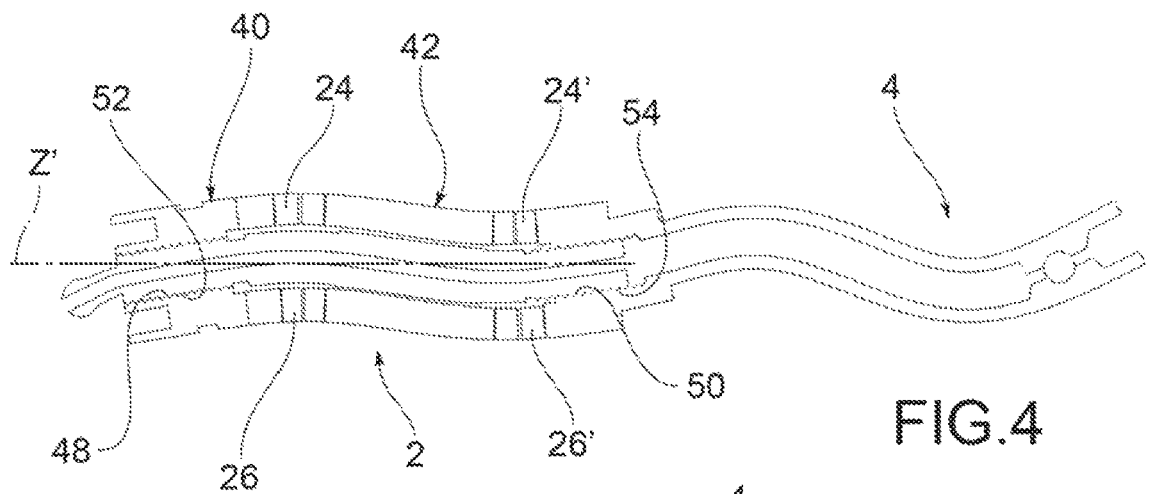
FIGS. 4, 6 show two longitudinal sectional views of an ultrasonic system according to a further embodiment, in two successive operating instants in a resonance vibratory cycle, these instants being in particular out of phase by about 180°.
Figure 5:
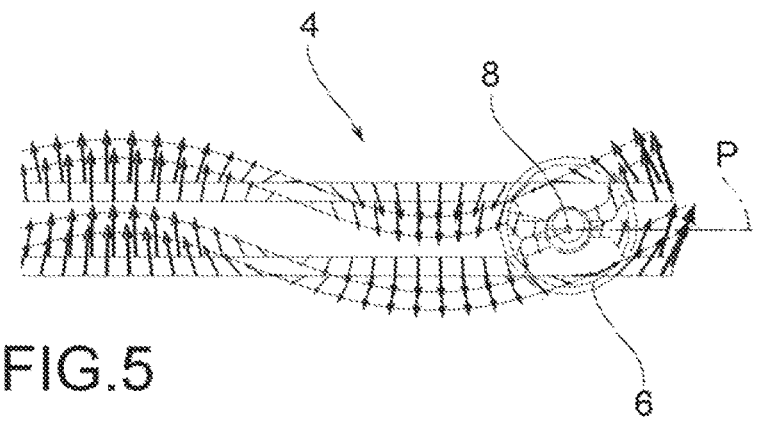
FIGS. 5, 7 show two schematics of the modal forms relating to the waveguide means and to the operating element in the instant in FIG. 4 and in FIG. 6, respectively, in the presence of the operating element.
Figure 6:
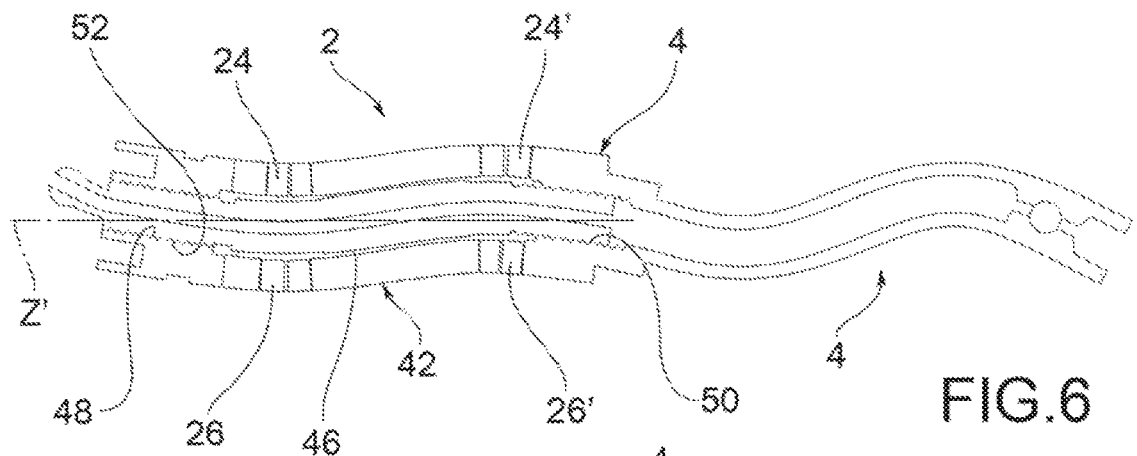
Figure 7:
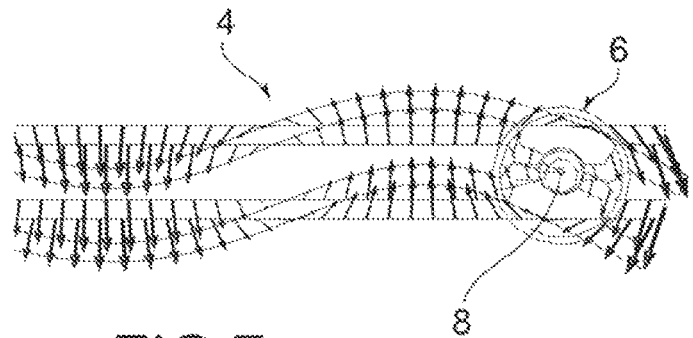
Figure 8:
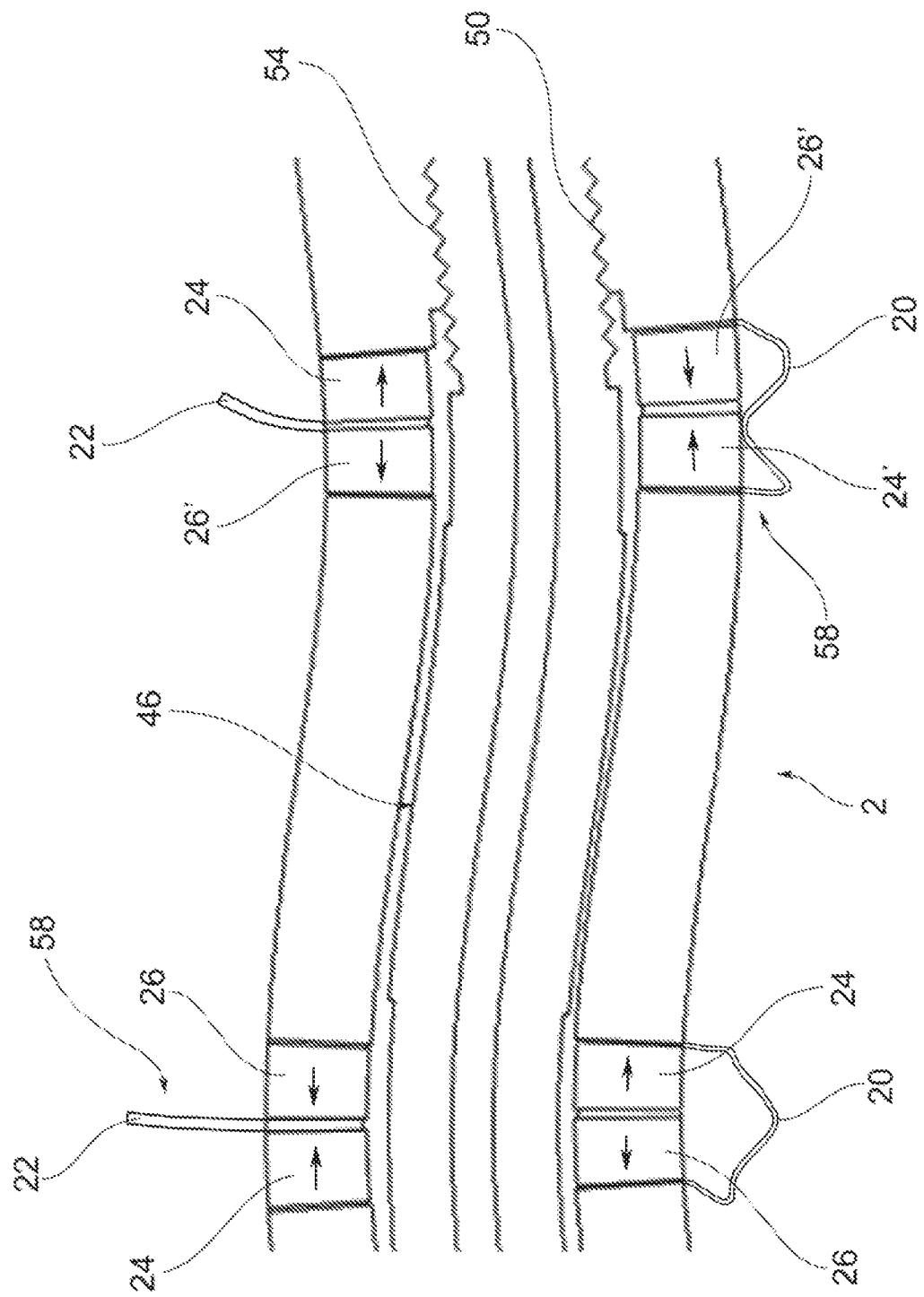
FIG. 8 shows an enlargement of a possible variant of the generator means in the area of the piezoelectric elements in which the vibrations are generated.

This phenomenon of contraction/expansion is for example well visible in the variants in FIG. 4, FIG. 6 or FIG. 8.

Taking as an example the instant in FIG. 4, it can be noted that in the first pair of left half-elements—according to the orientation of such a figure—the upper half-element 24 (which is in expanded condition) has an axial thickness slightly larger than the other half-element 26 of the pair, arranged below, which is in a contracted condition and therefore has a smaller thickness than the opposite element. Nevertheless, at the same time, another pair of half-elements 24', 26' placed on the right has an inverse condition due to the electric voltage supplied to the other pair.

More precisely, the pairs of half-elements have a position and a way of vibrating in flexion, which advantageously allows the ultrasonic system 1 to resonate.

As regards an instant before or after the one shown in FIG. 4, FIG. 6 shows an inverse configuration in which the expanded or contracted conditions of the discussed half-elements are exchanged, so as to create a repeated oscillation of the waveguide means 4.

According to an embodiment, the present system comprises control means 90 of the electric voltage applied to the generator means 2.

According to an embodiment, the control means 90 are configured so that the electrical voltage applied to a pair of piezoelectric elements (for example to a pair of adjacent elements) has the same module and the same phase.

According to an embodiment, the ultrasonic transducer 16, 74 comprises at least one pair of piezoelectric elements 18 placed axially side by side, for example along the assembly direction Z'.

According to an embodiment, within this pair of piezoelectric elements 18 (for example when included in the ultrasonic transducer 16), a half-element 24, 26 with a determined polarization direction is placed side by side in a radial direction and in the axial direction to half-elements with a polarization direction opposite thereto.

More precisely, in the pair of adjacent piezoelectric elements, the direction of polarization between radially adjacent half-elements (in particular: positioned symmetrically with respect to the assembly direction Z') is opposite, and the direction of polarization between adjacent half-elements in the assembly direction Z' is also opposite (more precisely: arranged on the same side along such a direction Z').

According to an embodiment, the half-elements 24, 26 are separated by an intermediate space 56 which extends in a substantially orthogonal plane with respect to the oscillation plane P.

According to an embodiment, the half-elements 24, 26 are made in the form of a circular or (semi-)annular sector, for example a half moon.

According to another embodiment, the piezoelectric element 18 (for example of the ultrasonic transducer 16), or the plurality of such elements, is made in an annular shape comprising two element portions having polarization of mutually opposite direction (specifically: positioned symmetrically with respect to the assembly direction Z'), and an intermediate portion without polarization.

Figure 19:
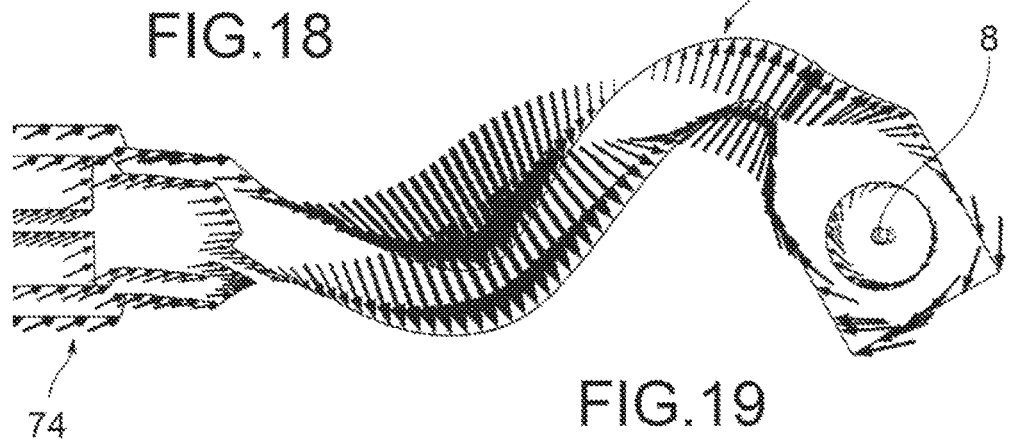
FIGS. 19, 21 show two schematics of the modal forms relating to the waveguide means and to the operating element in the instant in FIG. 18 and in FIG. 20, respectively.
Figure 21:
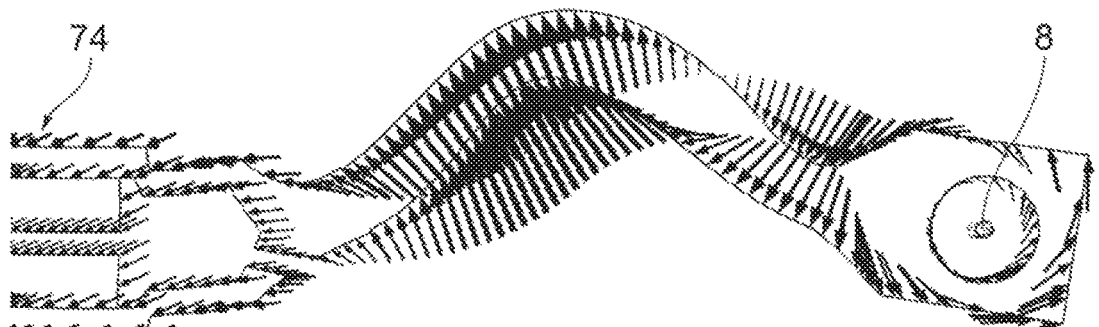
Figure 22:
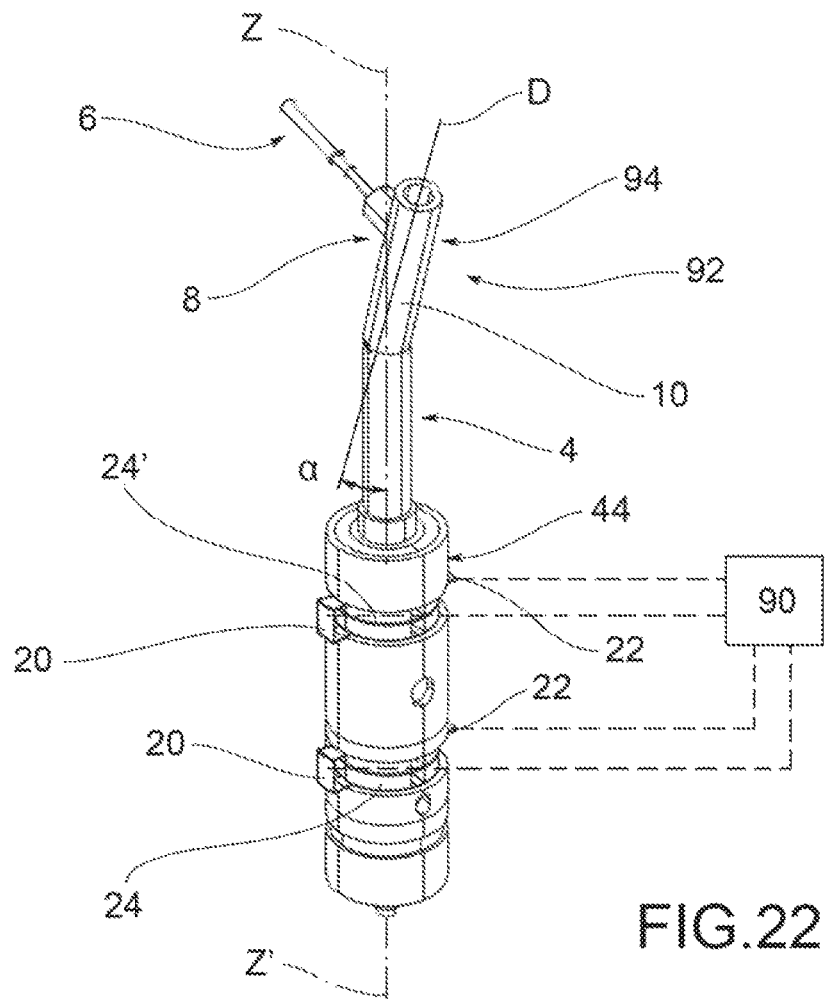

As regards the features of the longitudinal ultrasonic transducer 74, such a transducer is not configured to vibrate in a single plane as the variant just discussed. On the contrary, such a transducer 74 is configured to generate longitudinal microvibrations (i.e. along the assembly direction Z' and/or along the prevailing development direction Z; for example, see the direction of the arrows in FIG. 19 or 21 which have a main longitudinal component in the prevailing development direction Z) and alternating, so that these are transmitted to the waveguide means 4.

According to an embodiment, the piezoelectric elements 18 (for example of the ultrasonic transducer 74 of the longitudinal type) are made in an annular or tubular shape.

According to an embodiment, the ultrasonic transducer 74 comprises at least one pair of piezoelectric elements 18, with mutually opposite polarization directions and parallel to the assembly direction Z'.

The waveguide means 4 are connected to and extend away from the generator means 2 so as to bend (and advantageously resonate) at least in part.

It should be noted that the expression "bend at least in part" means a bending that substantially concerns all the waveguide means 4 (as for example schematized in FIG. 4-7 or 14-17), or a bending concerning exclusively a part (for example see the reference numeral 28 in FIG. 19 or 21) of such means.

According to an embodiment, the generator means 2 are configured to bend the waveguide means 4 in a single oscillation plane P, by means of stationary ultrasonic microvibrations.

In other words, according to this embodiment, the waveguide means 4 are susceptible to be bent by the microvibrations generated by the generator means 2 (and advantageously to resonate due to these microvibrations), so that the oscillations of the waveguide means 4 are stationary with at least one stationary bending node 8.

It should be noted that, in this description, the expression "stationary node" means at least one orthogonal segment (with respect to the prevailing development direction Z) of the waveguide means 4 characterized by the absence of micro-oscillation or microvibration.

Specifically, the flexural vibration discussed above takes place at a frequency corresponding to a bending frequency of the generator means, for example at a bending resonance frequency, such a frequency being able for example to be set through control means 90 (for example electronic) of the generator means 2.

The operating element 6 is joined or jointed to the stationary bending node 8, so that the flexural microvibrations are transmitted by the waveguide means 4 to the operating element 6 as alternate torsional or flexural microvibrations.

In other words, the bends induced by the generator means 2 are transmitted to the operating element 6 so that the latter vibrates in an alternating/reciprocating manner in a torsional or flexural manner.

Figure 3:
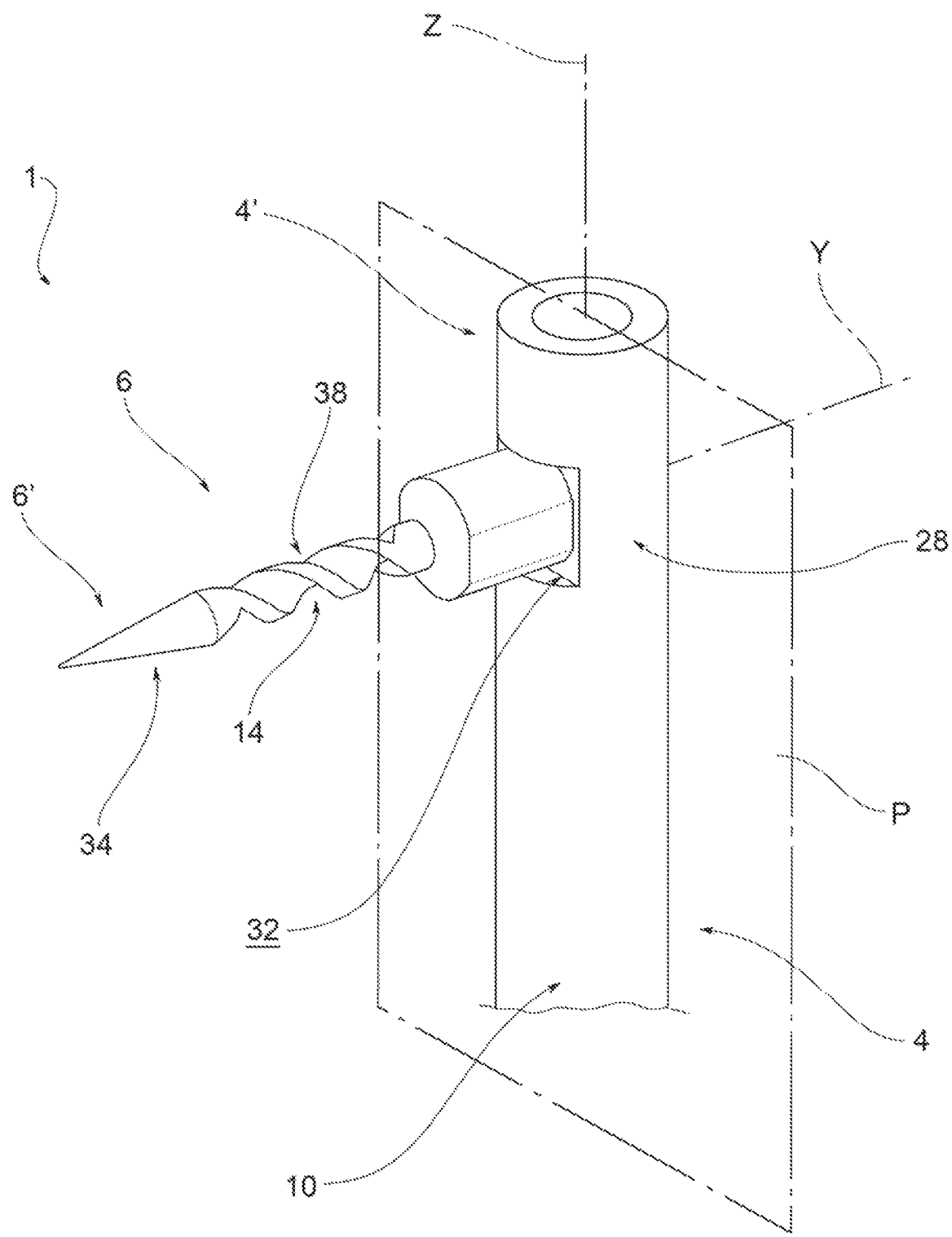
FIG. 3 illustrates an ultrasonic system according to the present invention, according to a second possible embodiment, in a perspective view in a non-operating configuration.
Figure 10:
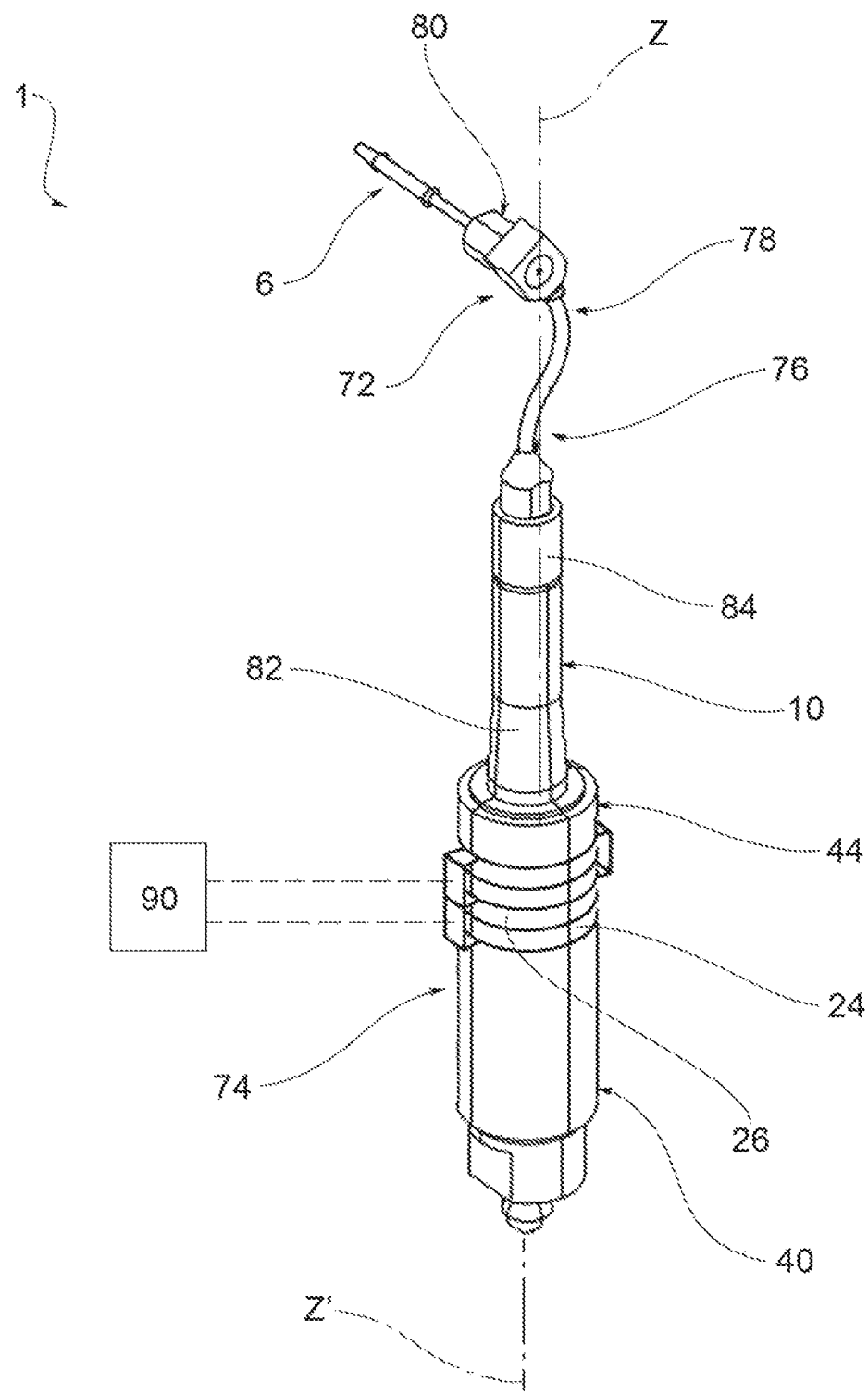

According to an embodiment, see for example FIG. 2A, FIG. 3 or FIG. 10, the operating element 6 develops outside the oscillation plane P so that the flexural microvibrations are transmitted as torsional microvibrations alternating with such an element 6.

Figure 9:
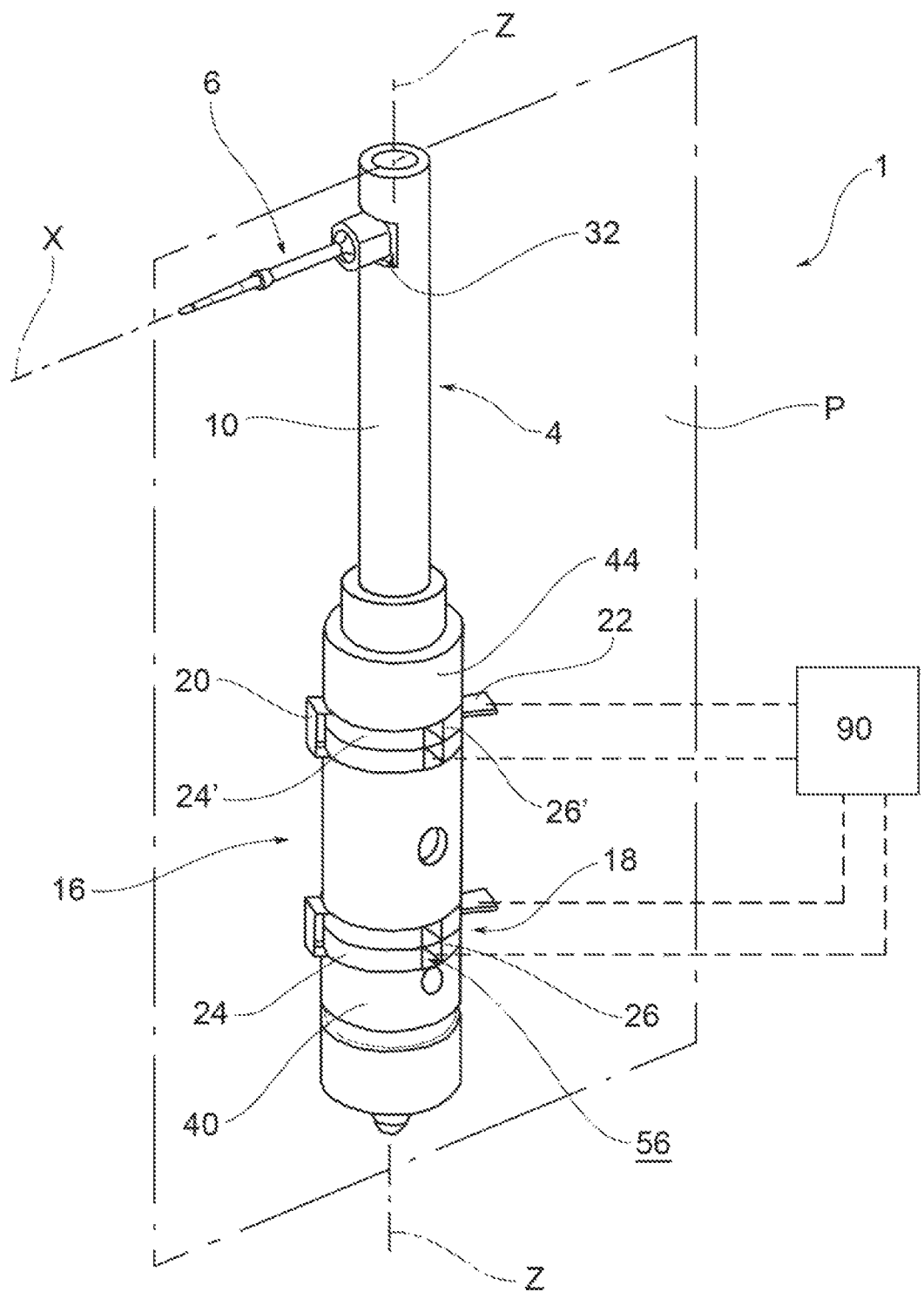
FIGS. 9, 10 show perspective views of ultrasonic systems, object of the present invention, according to other possible variants.

According to an embodiment, see for example FIG. 9, the operating element 6 develops in a substantially parallel, optionally coincident, plane with respect to the oscillation plane P so that the flexural microvibrations are transmitted as flexural microvibrations alternating with such an element 6.

According to an embodiment, the generator means 2 are configured to generate longitudinal microvibrations, transmitted along the waveguide means 4 in the prevailing development direction Z.

According to an embodiment, the waveguide means 4 distally comprise an element-carrying body 72 connected to the operating element 6 (for example to a base 62 thereof) and at least one guide loop 28, which develops radially with respect to the prevailing development direction Z. In this way, the element-carrying body 72 and the guide loop 28 are configured to transform the longitudinal microvibrations into torsional microvibrations to the operating element 6.

In other words, the guide loop 28 causes the longitudinal microvibrations of the generator means 2 to degenerate into flexural microvibrations, which will be suitably converted into alternating torsional microvibrations by the element-carrying body 72.

According to an embodiment, the element-carrying body 72 defines the stationary bending node 8.

According to an embodiment, the guide loop 28 is connected (for example rigidly) at a first end 76 to a guide body 10, in the following also defined as waveguide body 10, of the waveguide means 4, and at an opposite second end 78 to the element-carrier body 72.

According to an embodiment, the guide body 10 comprises a proximal portion 82 and a distal portion 84, releasably joined together.

It should be noted that, in the present description, the term "distal" means the components positioned at, or facing towards, the operating element 6; on the other hand, the term "proximal" means the components positioned on the opposite side with respect to such an element 6, specifically towards a mass body 40 arranged at an axial end of the transducer 16, 74.

Figure 18:
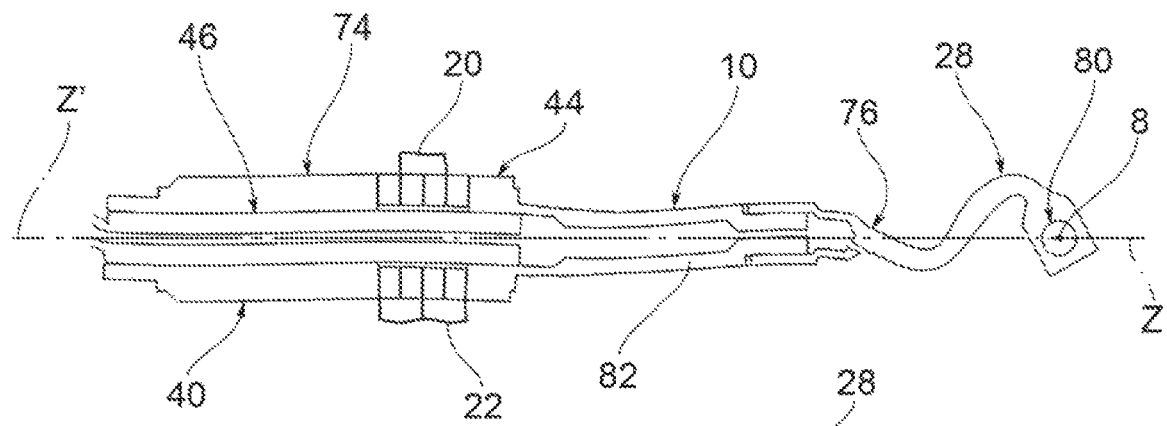
FIGS. 18, 20 show two longitudinal sectional views of the ultrasonic system according to the embodiment in FIG. 10, in two successive operating instants in a resonance vibratory cycle, these instants being in particular out of phase by about 180°.
Figure 20:
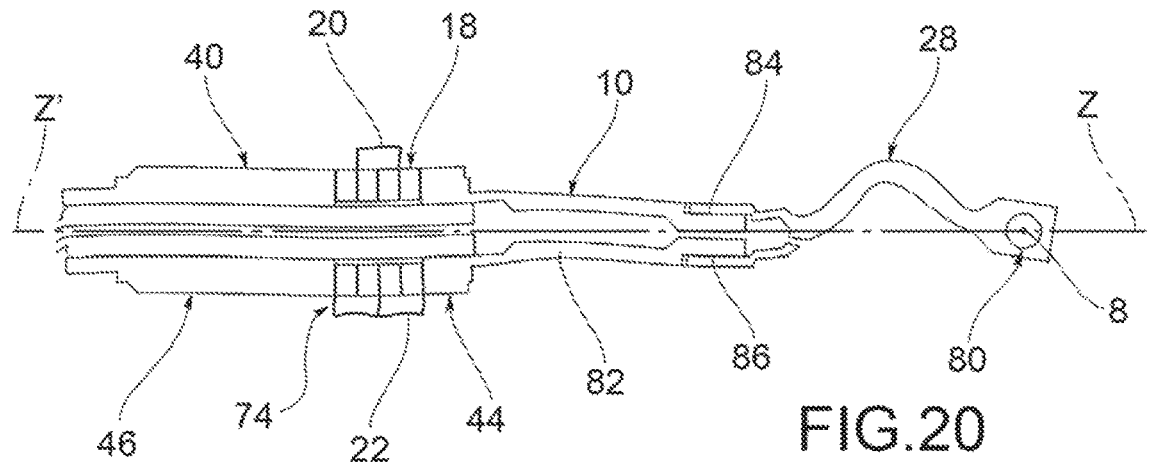

According to an embodiment, the releasable connection between the proximal portion 82 and the distal portion 84 is implemented by means of a bayonet connection or, as for example schematized in FIG. 18 or in FIG. 20, with a threaded connection 86.

According to an embodiment, the proximal portion 82 and the distal portion 84 are geometrically coupled, for example with a male-female coupling.

According to an embodiment, the distal portion 84 defines a female portion, in which a proximal male portion 82 is at least partially inserted.

According to an embodiment, the distal portion 84, the guide loop 28 and optionally the element-carrier body 72 are made in a single piece.

According to an embodiment (not shown), the stationary bending node lies in the prevailing development direction Z (specifically in a non-operating condition of the generator means 2).

According to an embodiment, the stationary bending node 8 is staggered radially with respect to the prevailing development direction Z (specifically in a non-operating condition of the generator means 2).

According to an embodiment, the generator means 2 and the waveguide means 4 are received in a substantially complete manner in the oscillation plane P.

According to an embodiment, the generator means 2 and the waveguide means 4 are aligned along a prevailing development direction Z of the waveguide means 4.

According to an embodiment, the guide body 10 constitutes an extension (specifically: an axial extension) of the connecting stem 46.

According to an embodiment, the waveguide means 4 are capable of bending at least in part or of resonating together with the generator means 2.

The operating element 6 is joined or jointed to the stationary bending node 8, so that the flexural microvibrations are transmitted by the waveguide means 4 to the operating element 6 as alternate torsional or flexural microvibrations.

Specifically, the transmission of the flexural microvibrations from the waveguide means 4 to the operating element 6 occurs by means of a dynamic torque parallel to the oscillation plane P (optionally received in such a plane P) and with a fulcrum in the stationary bending node, acting on the base 62 of the operating element 6, so as to generate the torsional or flexural microvibrations.

According to an embodiment, such a transmission occurs without the microvibrations of the operating element 6 influencing, by alternating the modal shape or the amplitude, the microvibrations of the generator means 2 and/or of the waveguide means 4, and vice versa.

It follows that the flexural microvibrations of the waveguide means 4 can be transformed into alternating torsional microvibrations or into alternating flexural microvibrations. For example, the different torsional/flexural transformation may depend on the different coupling seat 30, 32, 80, defined by the waveguide means 4, engaged by the operating element 6.

According to an embodiment, the waveguide means 4 comprise at least one guide body 10, for example of a substantially tubular or cylindrical shape.

According to an embodiment, the guide body 10 has a substantially constant cross-section throughout the entire length thereof.

According to an embodiment, the guide body 10 has at least one tapered cross-section in the distal direction. For example, the distal portion 84 could be tapered distally.

According to another embodiment, the guide body 10 has a variable cross-section, for example increasing or decreasing away from the generator means 2, for example in order to amplify or dampen the microvibrations passing through such a body 10 depending on the needs.

According to an embodiment, the guide body 10 has a substantially circular cross-section.

According to an embodiment, the operating element 6 is rigidly joined to a body 10, 72 of the waveguide means 4, at the stationary bending node 8.

It should be noted that, in the present description, the expression "body 10, 72" means "guide body 10" or "element-carrier body 72" according to the embodiments that require the use of one or of the other of the mentioned bodies.

According to an embodiment, the operating element 6 is removably joined to a body 10, 72 of the waveguide means 4.

According to an embodiment, the removable connection between the operating element 6 and the guide body 10 is implemented by complementary coupling threads 12 arranged on such an element 6 and on such a body 10.

According to an embodiment, the removable connection between the operating element 6 and the guide body 10 may comprise the above releasable union between the proximal portion 82 and the distal portion 84.

According to an embodiment, the removable connection between the operating element 6 and the guide body 10 is implemented by means of a locking element 60, for example a dowel, coupled to the guide body 10 (optionally by means of coupling threads 68, 70 complementary to each other).

According to an embodiment, the guide body 10 may delimit at least one element seat 66 for at least partially accommodating (for example: completely) the locking element 60.

According to an embodiment, the locking element 60 or dowel acts in compression on an abutment surface 64 delimited by the operating element 6, specifically defined by the base 62 thereof.

According to an embodiment, the abutment surface 64 is substantially planar, or concave.

According to an embodiment, the operating element 6 extends along a secondary direction Y incident or substantially orthogonal with respect to the oscillation plane P.

According to an embodiment, the secondary direction Y implements a symmetry axis of the operating element 6.

According to an embodiment, the secondary direction Y intersects the oscillation plane P in the stationary bending node 8.

According to an embodiment, the secondary direction Y lies in an element plane S orthogonal to the oscillation plane P.

According to an embodiment, the operating element 6 develops at least in part along a tertiary direction X substantially parallel to, optionally received in, the oscillation plane P.

According to an embodiment, the tertiary direction X implements a symmetry axis of the operating element 6.

According to an embodiment, the operating element 6 is connected to the waveguide means 4, or to a body 10, 72 of said means 4, through at least one transmission body 14, for example integrated in the or applied to the operating element 6.

According to an embodiment, the transmission body 14 may be made in a single piece with the operating element 6.

According to an embodiment, the transmission body 14 may be mounted to the operating element 6, for example in a releasable manner.

According to an embodiment, the transmission body 14 is designed to merely transmit the microvibrations from the generator means 2 to the operating element 6, without however altering in any way the frequencies of such microvibrations.

According to an embodiment, the transmission body 14 is configured and/or tuned to amplify, or on the contrary dampen, the microvibrations received from the generator means 2.

According to an embodiment, the operating element 6 develops, or the operating element 6 and the transmission body 14 develop, away from the waveguide means 4 by a length L (see for example FIG. 11) comprised in a neighborhood I of a quarter, or a multiple integer n thereof, of the $\lambda$ the torsional or flexural microvibrations generated in the operating element 6 (said neighborhood I being less than or equal to $n*\lambda/10$, preferably $\lambda/10$ and even more preferably $\lambda/40$).

According to an embodiment, the length L is measured along the secondary direction Y or along the tertiary direction X.

According to an embodiment, the waveguide means 4 (or a guide body 10 thereof) comprise distally an asymmetrical portion 92 (for example a folded or inclined portion) with respect to the prevailing development direction Z, the stationary bending node 8 being arranged at such an asymmetrical portion 92.

According to an embodiment, the waveguide means 4 (or a guide body 10 thereof) comprise an inclined section 94 which extends along an incident direction D with respect to the prevailing development direction Z, with a predetermined angle of incidence a.

According to an embodiment, the angle of incidence a is an acute angle.

According to an embodiment, a distal end 4' of the waveguide means 4 defines one or more radial coupling seats 30, 32 for the connection of the operating element 6.

According to an embodiment, the waveguide means 4 delimit two radial coupling seats 30, 32 oriented so that the tertiary direction of an operating element 6 in a seat 30 is incident or substantially orthogonal with respect to the secondary direction Y of an operating element 6 engaged in the other seat 32.

More precisely, each coupling seat 30, 32 is configured for the connection (for example for the releasable connection) of an independent operating element 6 to the ultrasonic system 1.

According to an embodiment, the complementary coupling threads 12 may be arranged at a radial coupling seat 30, 32.

For example, one or more coupling seats may comprise a seat cavity 88 which extends towards the inside of the guide body 10 (that is to say, at least partially in the thickness of such a body 10), in which the above complementary coupling threads 12 are arranged.

According to an embodiment, the operating element 6 comprises a helical stem 38 which develops helically along the secondary direction Y, so that a distal portion 6' of the operating element 6 is susceptible to oscillate in percussion, with a longitudinal component and alternating along the secondary direction Y.

In other words, this variant provides that the torsional microvibration applied to the asymmetry of the helical stem 38 produces a micro-percussion along the secondary direction Y.

In other words, the distal portion 6' of the operating element 6 according to this variant is capable of acquiring a further percussive oscillation, with a longitudinal and alternating component along the secondary direction Y, in addition to the torsional oscillation.

According to an embodiment, the ultrasonic system 1 comprises control means 90 of the generator means 2, configured to control a frequency of the ultrasonic microvibrations of such means 2 at values such that the microvibrations of the operating element 6 are in the frequency range of 20-60 KHz, for example 20-36 KHz. In this way, part of mineralized structures (e.g. teeth or bones) can be selectively removed (or pierced) while preserving the integrity of lower density tissues (for example, soft tissues).

Innovatively, the ultrasonic system object of the present invention allows brilliantly solving the drawbacks related to the prior art.

More precisely, the present invention allows providing a working action, for example of drilling, through a reciprocating torsional or flexural movement of the operating element, renouncing the merely rotating action typical of the instruments used in the prior art, with obvious operative and possibly clinical advantages.

Advantageously, unlike conventional devices, the present ultrasonic system does not use micromotors which are associated with macroscopic vibrations.

Advantageously, the present ultrasonic system gives a high versatility of use, since the operating element can indifferently perform drilling or removal operations depending on the orientation of the seat engaged by such an element.

Advantageously, the present ultrasonic system gives a high versatility of use due to the geometry and features of the selected operative part.

Advantageously, the present ultrasonic system allows obtaining a greater tactile sensitivity and a greater intra-operative precision since the forces exerted, required by the operator, are considerably reduced.

Advantageously, the present ultrasonic system exploits ultrasonic microvibrations of the operating element, which produce holes or removals of material through a process of micronization of the removed material or tissue, which is then removed immediately by the mechanical action of the possible irrigation fluid present.

In any case, advantageously, the discussed reciprocating movement favors the removal or natural release of material debris.

Advantageously, in the present ultrasonic system the effects of centrifugal superheating are less extensive than (or even minimized with respect to) those produced by the macrovibrations generated by the rotation of the traditional bits/mills.

Advantageously, the present ultrasonic system allows achieving an improved stability of the operating element at the beginning of the drilling or removal of material.

Advantageously, the present ultrasonic system allows obtaining a markedly higher operating precision than conventional rotary tools (for example with respect to drill bits); the latter are in fact unstable at the beginning of the drilling due to a centrifugal component, which causes the tool to deviate from the desired drilling axis. In fact, according to the prior art and in particular in the field of implant surgery, a specially configured tip is used at the beginning to engage the bone surface to be drilled (the most common known as rose tip and lance cutter).

On the contrary, in conjunction with its microvibrating operation, the particular configuration of the operating element according to the invention allows imparting greater stability not only due to the substantial elimination of any centrifugal component for starting the tool.

Advantageously, in the present ultrasonic system it is possible to obtain a greater cleaning of the operating element-substrate interface, and a possible improvement of the osteo-regenerative processes (for the variants which provide for a surgical, implant or dental use of the system described herein).

Advantageously, the ultrasonic microvibrations to the operating element cause cavitation of any fluids that may be present (for example an irrigation fluid), allow the removal of bone debris from the side walls of the hole made by this element, leaving the aforementioned interface clean also by virtue of a washing of the walls of the hole generated by the ultrasonic system. In this way, the traditional bone smear layer, caused by the helicoidal tips and the conventional drills, is not formed, thus favoring the osteo-regenerative processes.

Advantageously, in the present ultrasonic system a selective drilling of the bone tissues is obtained through the use of low frequency vibrations. In fact, the vibrations at the selected frequency prove to be extremely advantageous to carry out drilling or removal of mineralized structures, for example of bones or teeth, but they are ineffective when applied to the soft tissues.

Therefore, advantageously, an accidental contact with the soft tissues, of lower density, does not cause any damage or tear, but only a transient and limited release of heat.

Advantageously, the dynamic features of the generator means and of the waveguide means are only marginally influenced by the nature of the operating element (for example, by the mass, the geometry and/or longitudinal and/or transverse encumbrance thereof), since such an element is fixed at a stationary node, and therefore such a nature is substantially irrelevant to the generation and maintenance of the microvibratory movement.

Also the nature and the dynamic features of the generator means and of the waveguide means (for example the mass, the geometry and/or the longitudinal and/or transverse encumbrance of the waveguide means and/or of the generator means) do not influence, or only marginally influence, the oscillation of the operating element, except for the transmission of the desired microvibrations.

This circumstance therefore makes the present ultrasonic system particularly versatile in the design and use of the operating elements that can be associated with the present system.

Advantageously, the present system has been designed to operate at a fixed frequency, so as to generate predetermined stationary bending nodes always located in the same axial position of the generator means and the waveguide means.

According to a further advantageous aspect, although the frequency of the fixed generator means remains, the configuration of the operating element (for example the length L, the section, the material, or the like thereof) may be adjusted according to need, in particular by intervening in the design step on the features of this element, tuning it to an appropriate harmonic of the microvibration.

By way of example, if it were necessary or advantageous to design an operating element of extremely small dimensions, it would be possible to obtain very large microvibration amplitudes thereof, defining a length L of the operating element equal to about a quarter of the wavelength of the excited microvibration.

Advantageously, a part of the operating element may act as an amplifier or as a damper for microvibrations.

Advantageously, the vibratory or resonance features of the operating element may be altered even at a time subsequent to the realization of the element itself, for example in order to amplify or dampen the microvibrations.

Advantageously, the present generator means have been designed to generate and transmit vibrations capable of bending the waveguide means in a single oscillation plane, in a reliable, continuous manner and with technical devices that are simple to implement.

Advantageously, the present generator means have been designed to easily package all the necessary components, with a (pre-)compression force that can be determined according to the needs.

Advantageously, the present system has been designed to allow operating elements of different shapes to vibrate, since the stationary node is a place characterized by the absence of movement in the direction of generation of flexural vibrations.

This last circumstance makes the present system particularly innovative in that, in contrast to an extremely widespread technical prejudice, the operating element is placed in the neighborhood of a place (the stationary node) in which no movement occurs.

In other words, although the stationary node has a non-moving point or line, its surroundings have a minimum movement, but still sufficient to allow the desired excitation of the microvibrations.

Advantageously, the operative elements that can be used in the present invention are extremely small, mainly due to the wavelengths discussed above.

Advantageously, the system object of the present invention allows exerting a micro-percussion action which facilitates the penetration of the operative element into the tissue to be drilled.

A man skilled in the art may make several changes or replacements of elements with other functionally equivalent ones to the embodiments of the above system in order to meet specific needs.

Also such variants are included within the scope of protection as defined by the following claims.

Moreover, each variant described as belonging to a possible embodiment may be implemented independently of the other variants described.

According to an embodiment, starting from the embodiment in which the transformation of flexural vibrations into torsional vibrations takes place due to the coupling in a stationary bending node, it is possible to provide variations of the piezoelectric transducer.

Figure 1B:
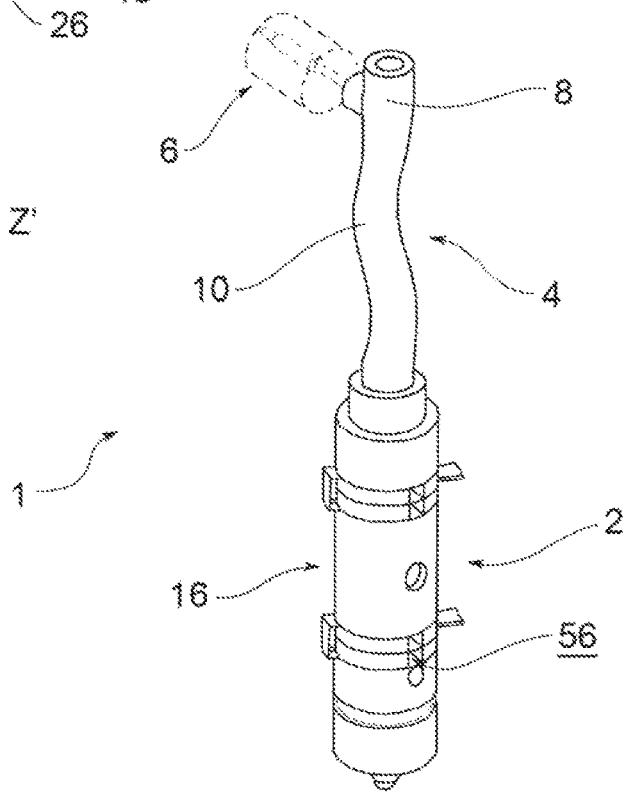

According to an embodiment, the transducer represented in its entirety in FIGS. 1 and 9 which in terms of shape, size and arrangement of the piezoelectric ceramics is a transducer capable of generating a flexural vibration in the waveguide means 4 (or waveguide body 10). Alternatively, a flexural vibration is obtainable by making a longitudinal vibration "degenerate" through a waveguide 4 provided with an asymmetry with respect to the longitudinal axis Z of the transducer itself. According to an embodiment, in FIG. 10 there is the representation of a longitudinal transducer (Langevin Type, 74) consisting of a piezoelectric package 24, 26, a mass body or a backing mass or tuner, 40, a waveguide or horn or concentrator 4, with a guide body 10 to which the vibration transformer (herein the loop 28) is coupled by means of a thread (threaded coupling 86) in which an element-carrying body 72 is present and, in coincidence of the stationary node 8, the coupling seat 80 for the operating element 6.

Also in this embodiment, the stationary bending node is on the prevailing development axis of the generator means Z providing for the connection to the stationary node of the operating element 6 and the orthogonality between the nodal plane (oscillation plane P) and symmetry axis of the operating element itself Y.

According to an embodiment, the prevailing development direction Z and the axis of the operating element 6 are incidents, substantially orthogonal, i.e. with an angle of between 85 DEG and 125 DEG, preferably 90 DEG, and belong to the same plane (i.e. there is no eccentricity).

According to an embodiment, an improved performance (vibration amplitude) in the distal part of the operating element 6 is obtained when the diameter d' of the waveguide 4 is greater than the diameter d of the stem of the operating element 6, and preferably if the diameter d' of the waveguide 4 is greater than or equal to half d/2 of the diameter of the stem of the operating element 6.

Figures 23, 24:
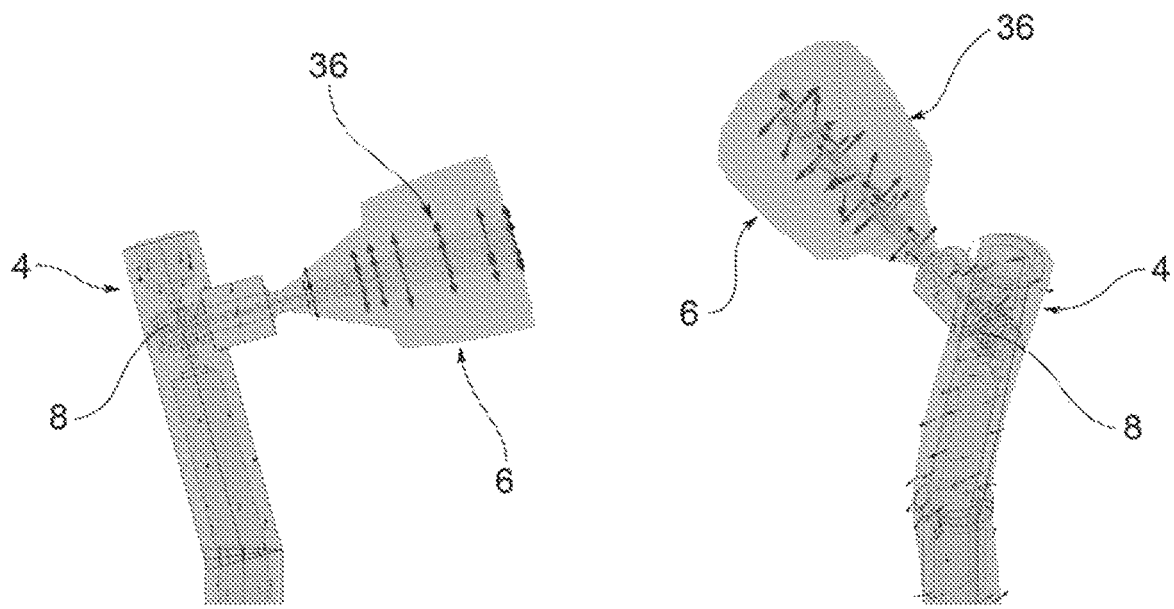
Figure 25:
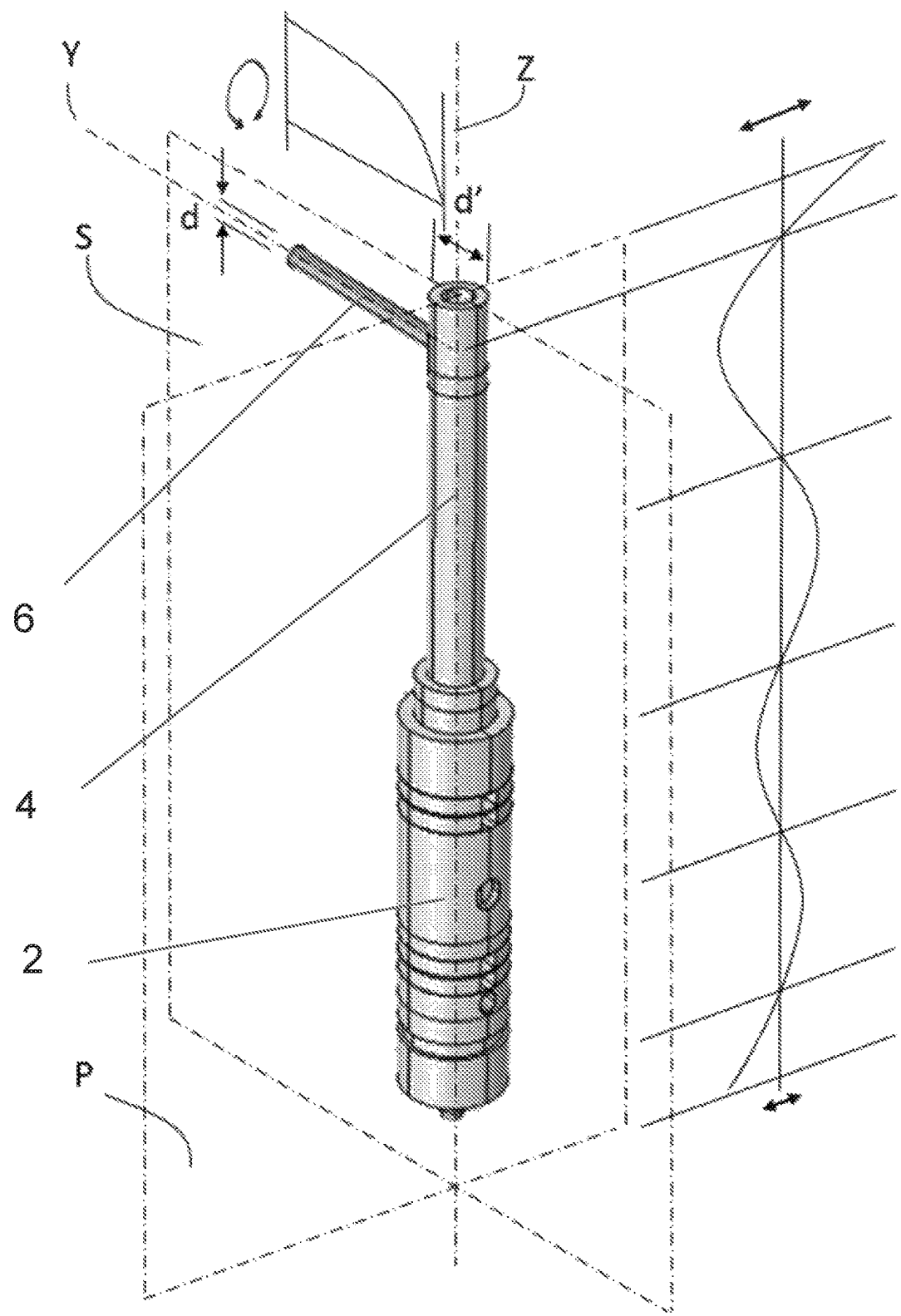
FIG. 25 is a perspective view of an ultrasonic system according to the present invention, according to the first possible embodiment in which the oscillation planes P of the guide body and the element plane S in which the operating element oscillates are highlighted, in which the vibrational deformation of the flexural ultrasonic transducer and of the waveguide means and the torsional deformation induced in the operating element are highlighted in a moment of maximum oscillation.
Figure 26:
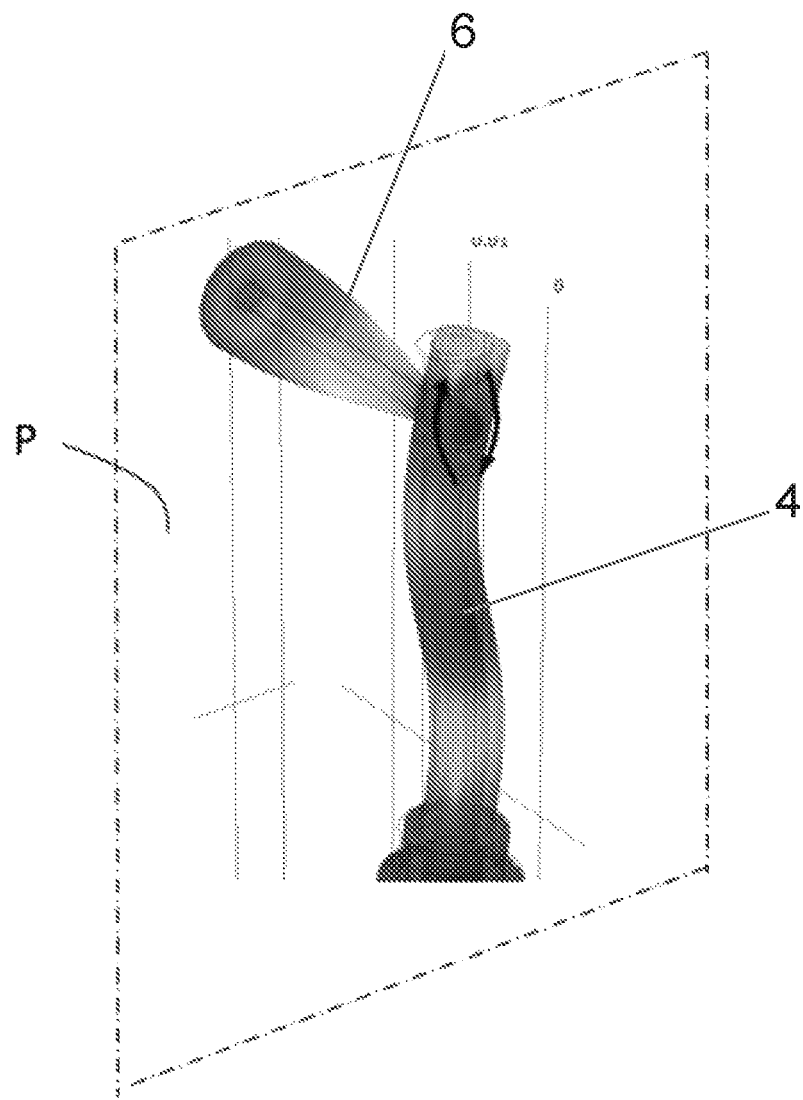
FIG. 26 is a perspective view of a detail of the solution in FIG. 25 in which the deformation of the ultrasonic system is shown in an amplified manner in an instant of operation in a vibratory resonance cycle.
Figure 27:
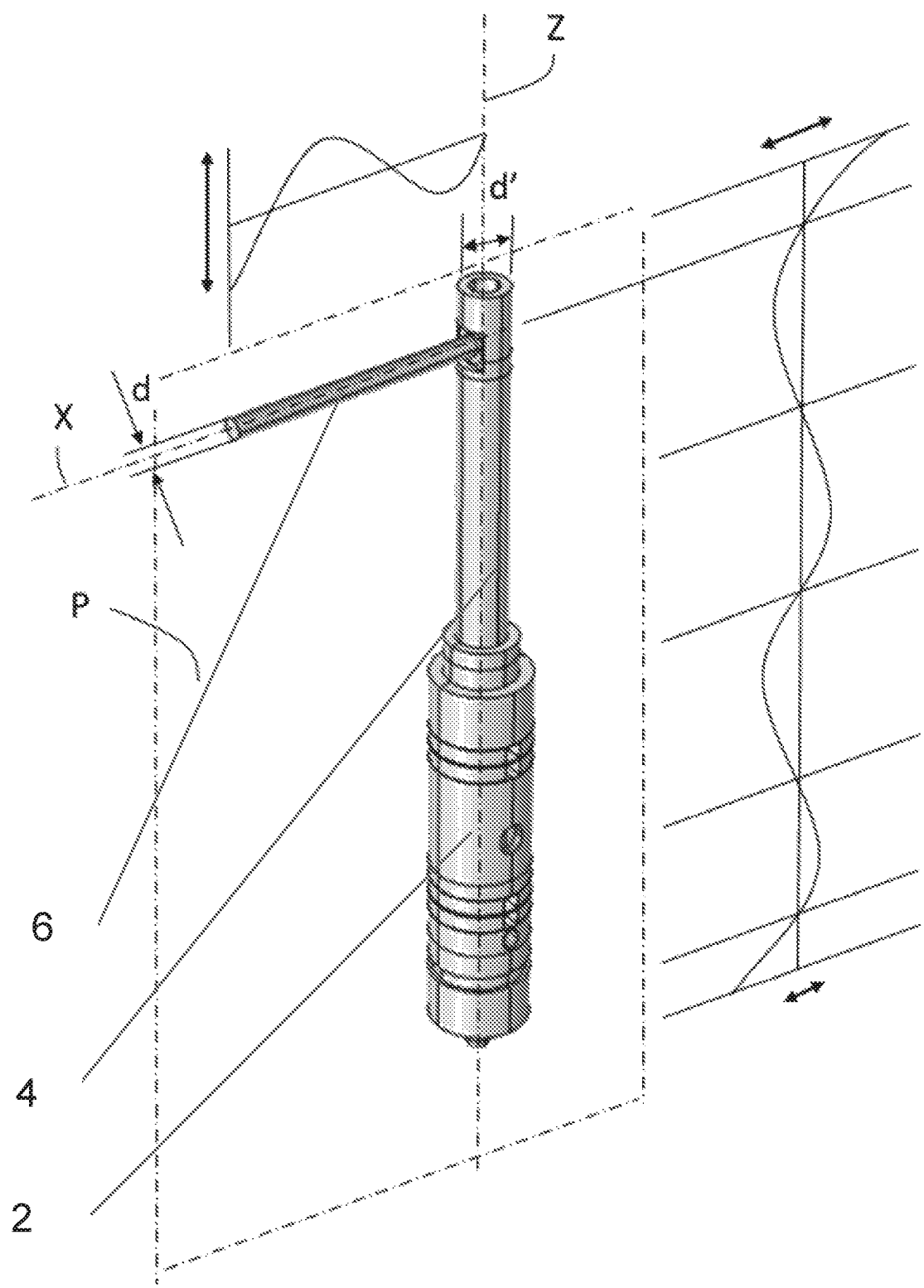
FIG. 27 is a perspective view of an ultrasonic system, object of the present invention, according to a further embodiment in which the operating element lies in the oscillation plane P of the flexural ultrasonic transducer and in which the vibrational deformation of the flexural ultrasonic transducer and of the waveguide means and the flexural deformation induced in the operating element are highlighted in a moment of maximum oscillation.
Figure 28:
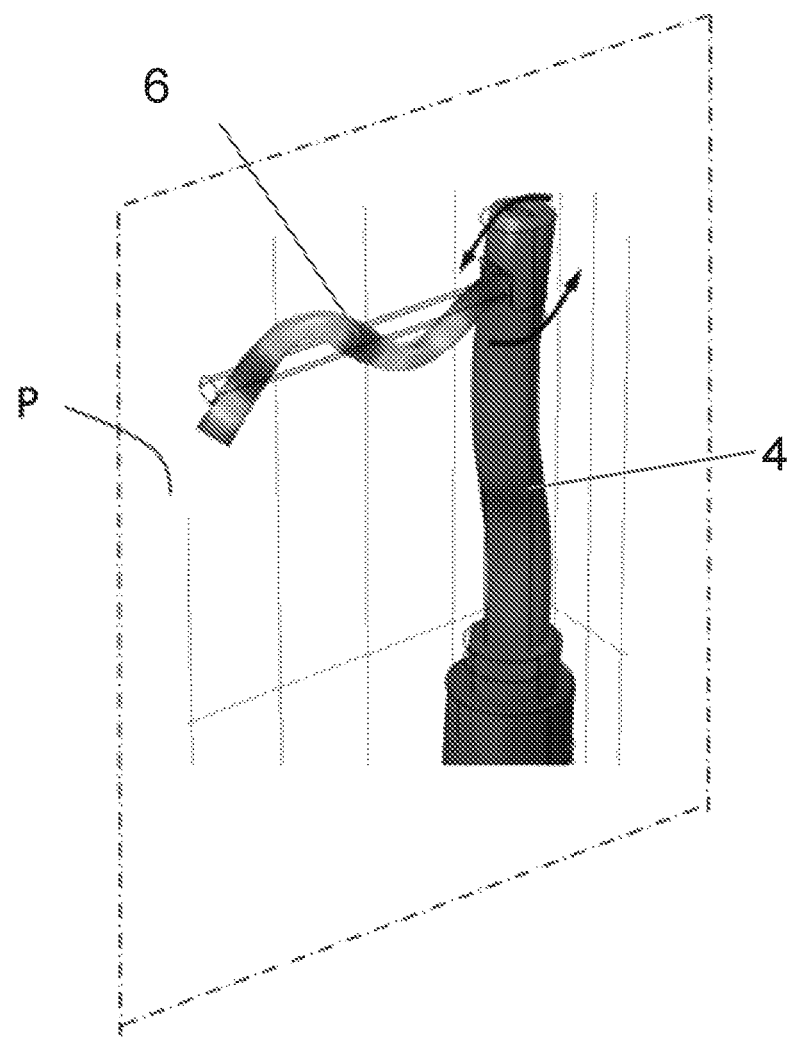
FIG. 28 is a perspective view of a detail of the solution in FIG. 27 in which the deformation of the ultrasonic system is depicted in an amplified manner in an instant of operation in a vibratory resonance cycle.

According to an embodiment, referring to FIGS. 24 and 25, the diameter of the stem d is that of the cylindrical operating element 6, while in relation to FIGS. 9, 10, 11, 12, 13 the diameter d is that of the transmission body 14. The base of the operating element 62 serves, for example, even if not solely, for the coupling, for example the screwing, of the operating element 6 to the distal portion of the waveguide 4.

According to an embodiment, a solution is proposed in order to increase the intraoperative visibility in the area of the oral cavity which includes the first and second molar (both at the mandibular and maxillary level), a visibility which is limited due to the size of the mouth and the variability between each patient with respect to the mouth opening.

To overcome this problem, micromotors provided with contra (i.e. the part of the twist drill to which the operating element is connected) are used today with the distal part reclined with respect to the main longitudinal axis of the contra itself. The angle of inclination of said distal part is typically 120° (30° considering the acute angle with respect to the prevailing development direction).

According to an embodiment, the distal part of the waveguide means 4 (or waveguide body 10) is inclined with respect to the prevailing development direction Z, without this embodiment affecting or compromising the transmission and transformation of the vibrations at the level of the operating element 6 (i.e. in such a way that the purely flexural vibration of the generator means 2 and waveguide means 4 is converted or transmitted in the operating element 6 connected to the stationary node in torsional vibration or in flexural vibration totally contained in the plane P, respectively).

According to an embodiment, in order to incorporate the desired inclination of the distal part of the waveguide means 4 or of the waveguide body 10 without compromising the transmission/transformation of the vibration in the operating element 6, a waveguide body 10 is provided having for example two development directions, which are defined proximal and distal considering the generator means 2. The proximal development direction is coaxial with the prevailing development direction Z while the distal part is inclined with respect to the prevailing development direction Z itself (direction D) by an angle α of between 5 and 45 DEG, preferably 30 DEG. In order to maintain the innovative features of the proposed ultrasonic system 1, the two development directions (Z and D) are also incident in a point corresponding to a stationary bending node of the waveguide means 4 or waveguide body 10. The axis D of the distal part of the waveguide means 4, and the axis (Y or X) of the operating element 6 continue to form an angle of between 85 DEG and 125 DEG, preferably 90 DEG.

Figure 11:
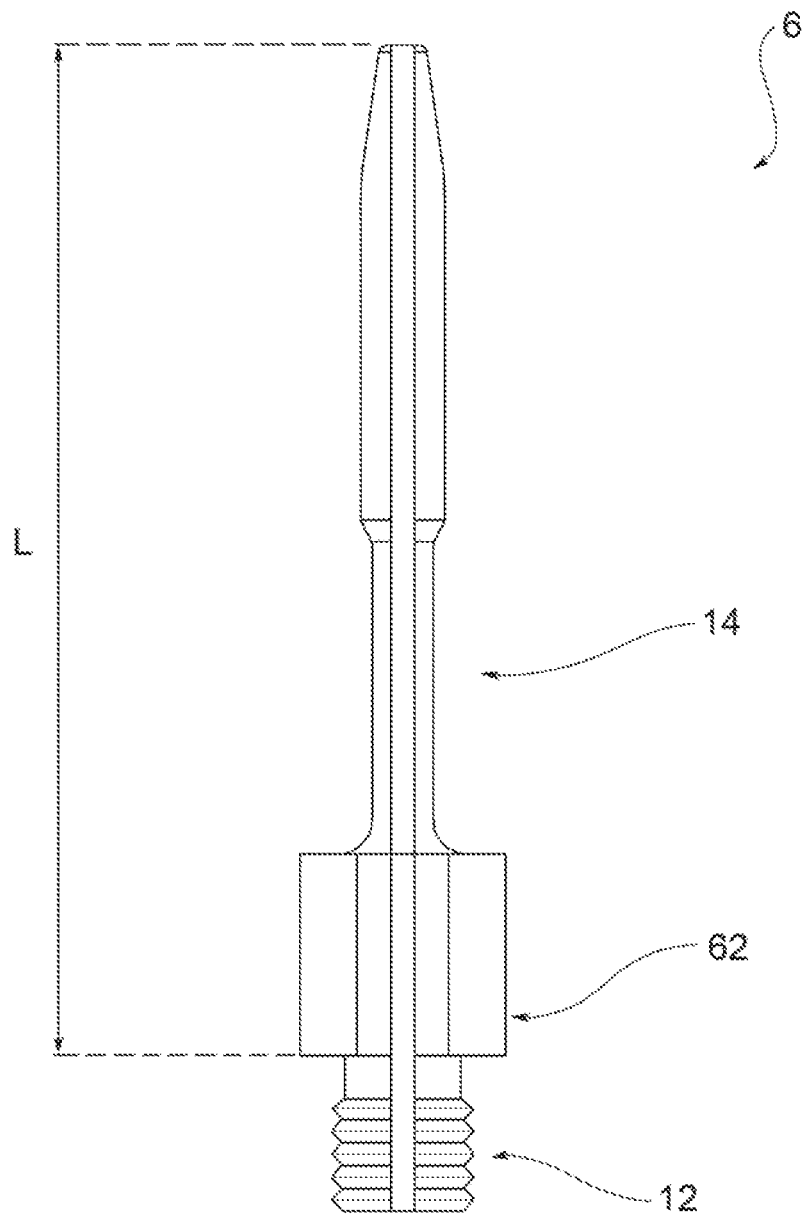
FIG. 11 shows a longitudinal section view of a possible configuration of the operating element.
Figure 12:
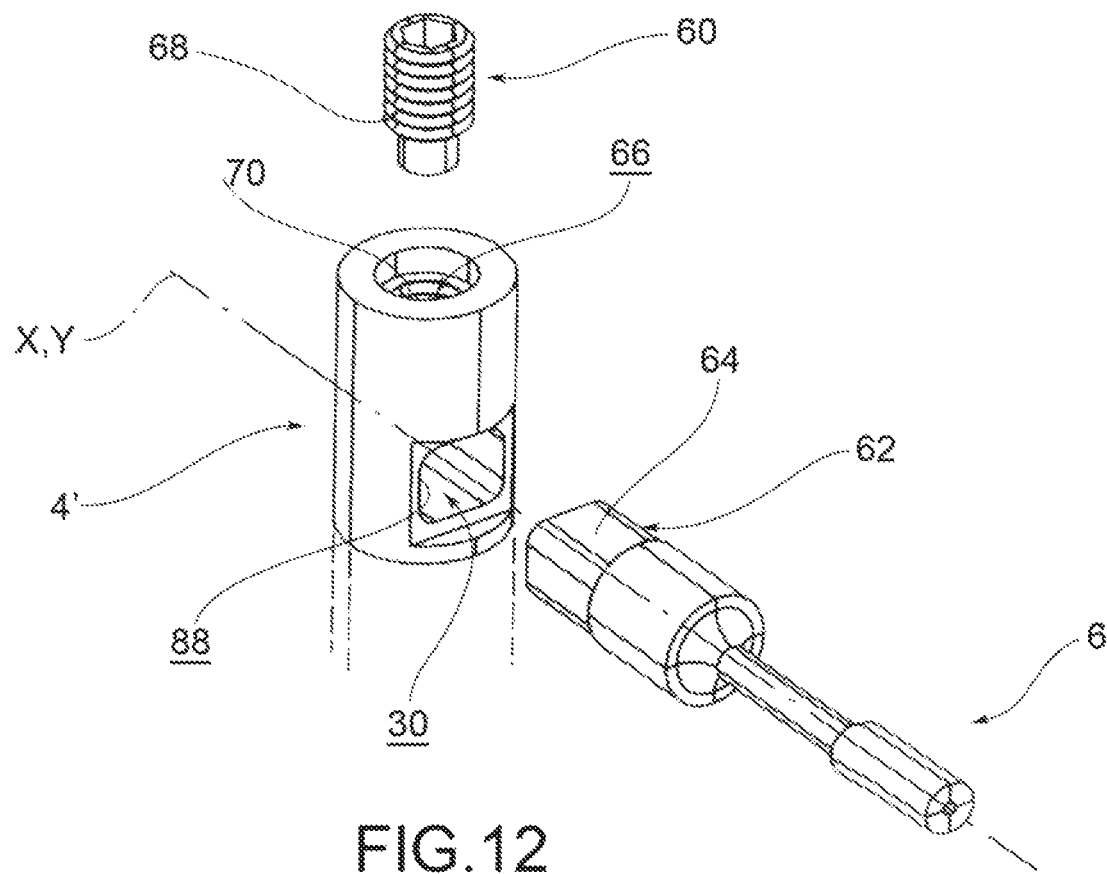
FIGS. 12, 13 illustrate two perspective views in separate parts of possible configurations of a distal portion of the waveguide means, respectively configured for the connection of a single operating element, or for the connection of an operating element in two different positions.
Figure 13:
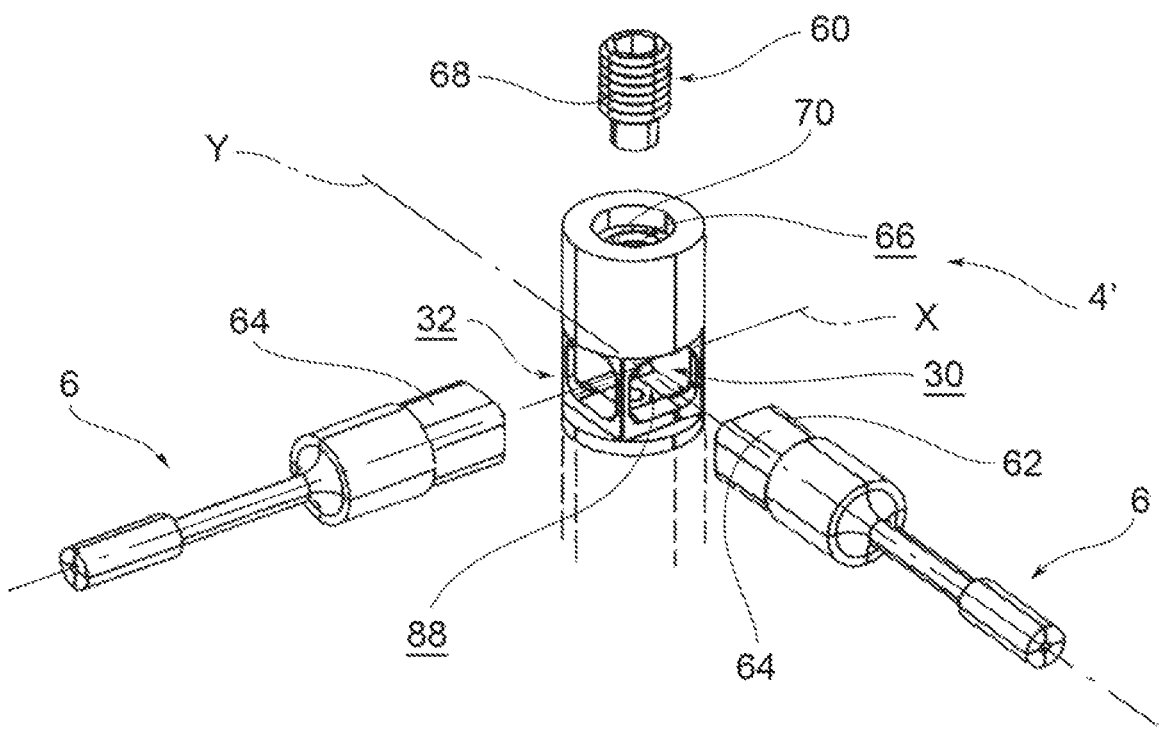
Figure 14:
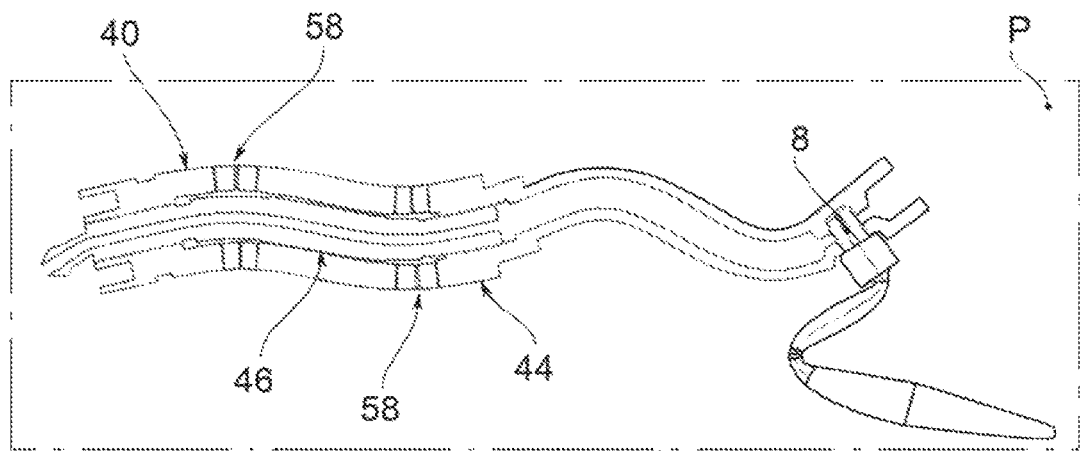
FIGS. 14, 16 show two longitudinal sectional views of the ultrasonic system according to the embodiment in FIG. 9, in two successive operating instants in a resonance vibratory cycle, these instants being in particular out of phase by about 180°.
Figure 15:
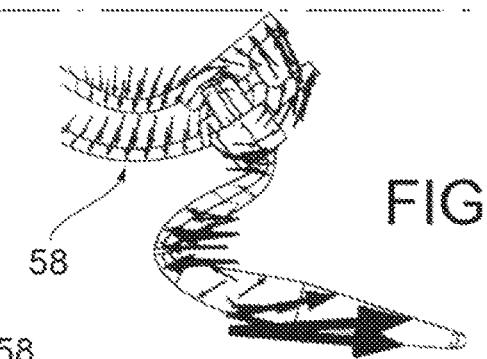
FIGS. 15, 17 show two schematics of the modal forms relating to the waveguide means and to the operating element in the instant in FIG. 14 and in FIG. 16, respectively.
Figure 16:
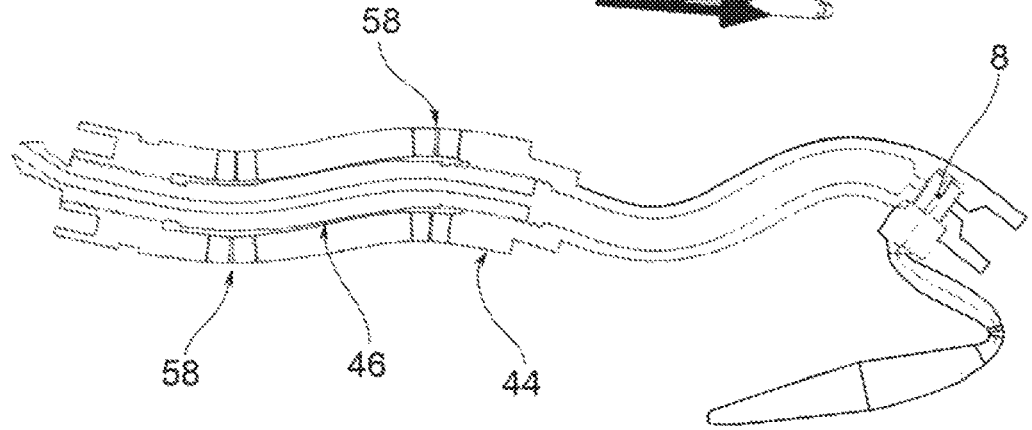
Figure 17:
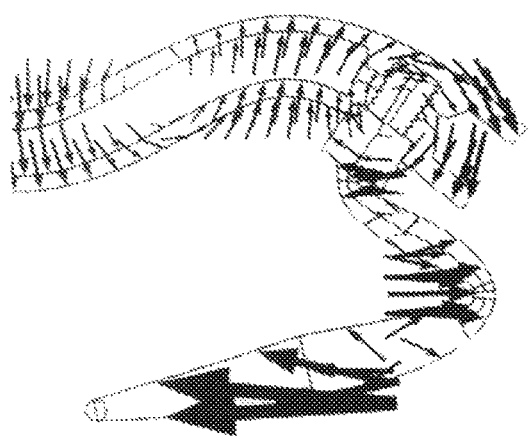

According to an embodiment, in order to have a considerable amplitude of vibration in the distal part of the operating element 6, the operating element 6 must have a diameter d, smaller than that of the waveguide 4, d', and preferably d≤½ d'. With reference for example to FIG. 11, the diameter of the operating element d corresponds to the diameter of the transmission body 14 of the operating element, while in FIGS. 25-28 these elements are represented simplified (cylindrical bodies) to facilitate understanding of the invention.

It is important that it is understood that using a stationary (flexural) node as a coupling point between two vibrating elements in order to transmit/transform the oscillation of the first element to the second (from waveguide and operating element) is substantially different from transmitting an oscillatory movement by coupling vibrating elements through a point/section of antinode (as for example is done in the prior art). Using an antinode is a conventional solution adopted in the ultrasonic power systems in which the point of maximum oscillation of a resonant component (the antinode in fact) is used as a source of excitation for a second resonant component coupled thereto, which in turn will exhibit a vibratory antinode at the coupling point/section. Since a stationary node is a minimum oscillation point, it is used in the prior art (for example in the ultrasonic power systems) as a coupling/anchoring point/section to isolate the vibrations of an oscillating element/device with respect to a structure coupled thereto (for example a handpiece or a case of any kind coupled to the vibrating ultrasonic system through flanges placed at nodal sections) that one does not want to oscillate. On the other hand, in ultrasonic power systems, using antinodes, not nodes, to transmit vibrations from one oscillating element to another is the only solution proposed.

On the other hand, thanks to the features of the present invention, in which families of modes, harmonics, and boundary conditions are suitably selected, a stationary node can be used as a point/section for the conversion/transmission of vibrations of considerable amplitude in the distal part of an operating element coupled to the waveguide.

The advantages deriving from the proposed configurations are: high vibrations of the operating parts useful for conducting operations in limited access spaces; reduced overall dimensions (operating element length proportional to λ/4 and not only to λ/2, as in known ultrasonic systems); almost no interference on the frequency and vibratory (modal) form of the system/oscillation generator joint by the operating element 6; greater geometric versatility for the design of the operating element; possibility of using a single joint of generator means 2 and waveguide 4 for the vibratory activation of a set (a plurality) of operating elements 6, each with specific geometrical and oscillatory features, without the coupling with such operating elements altering the electro-dynamic efficiency of the system.

A similar argument must be made in relation to the use of vibrating operating elements 6 of a length close to a quarter (or a multiple thereof) of the torsional/flexural wavelength generated in the element. Typically in ultrasonic power systems the length of the oscillating components is a half (or a multiple) of the wavelength of the generated vibration. Otherwise, thanks to the specific configurations proposed with this invention, as well as to the selected families of modes, harmonics and boundary conditions, it is possible to incorporate operating elements 6 of a length close to a quarter (or a multiple thereof) of the torsional/flexural wavelength generated (in the element), obtaining the aforementioned advantages, in particular high vibrations and reduced dimensions.

Thanks to the present invention, it is possible to obtain the transmission/conversion of flexural oscillations produced by the generator means 2 and transmitted with the waveguide 4 in torsional (or torsional-longitudinal), or flexural oscillations of the operating element 6 having a development axis incident and orthogonal, or almost orthogonal, with respect to the axis of the waveguide 4 and/or of the generator means 2.

The axes of the operating element, generator means and waveguide can be coplanar (therefore it is not necessary to carry out an eccentric assembly for the desired vibratory conversion/transmission).

Furthermore, the vibratory transmission/conversion takes place through the mechanical coupling of the operating element 6 in a bending node (and not through an antinode, as in the prior art) of the waveguide 4.

According to an embodiment, the waveguide 4 is absent and the coupling of the operating element 6 takes place in a bending node directly to the generator means 2.

According to an embodiment, the axes of the generator means 2 and waveguide 4 are incident and are not the same axis. The operating element 6 of the proposed invention functionally allows: (i) not to be mounted eccentrically with respect to the waveguide 4 (or to the generator means 2, if the waveguide 4 is not present); (ii) having a cross section (of diameter, d) smaller than the waveguide 4 of diameter d';

(iii) having a length proportional to λ/4 and not only to λ/2, as in all the components of the resonant system of the prior art.

Throughout this description, reference is made to oscillation planes of the system, referring to the planes containing the axes of the operating element 6 and of the generator means 2 and/or waveguide 4, clarifying that the coupling between vibrating elements is not eccentric as proposed in the prior art.

According to an embodiment, generator means 2 comprise two piezoelectric packets mutually rotated by 90° around the prevailing development direction/axis Z, and in which the connection of the operating element 6 takes place in a stationary bending node and the orthogonality is provided between the axes of the generator means 2 and/or waveguide 4 and the operating element 6 itself. Thanks to this configuration, it is possible to transmit the flexural vibrations generated in the transducer (or generator means 2) and in the waveguide 4 to the operating element 6 as torsional or flexural vibrations, depending on the piezoelectric packet being excited, allowing elimination of the double coupling seat for the operating insert 6 as described in FIG. 13.

LIST OF REFERENCE NUMERALS 1 ultrasonic system
2 generator means
4 waveguide means
4' distal end
6 operating element
6' distal portion of the operating element
8 stationary bending node
10 guide body or waveguide body
12 complementary coupling threads
14 transmission body
16 flexural ultrasonic transducer
18 piezoelectric element
20 contact electrode
22 contact electrode
24 half-element or part of element
24' half-element or part of element
26 half-element or part of element
26' half-element or part of element
28 guide loop
30 radial coupling seat
32 radial coupling seat
34 drilling bit
36 material removal cutter
38 helical stem
40 mass body
42 mass body
44 mass body
46 union stem or captive stem
48 first thread
50 first thread
52 second thread
54 second thread
56 intermediate space
58 antinode
60 locking element
62 base of the operating element
64 abutment surface
66 element seat
68 coupling thread
70 coupling thread
72 element-carrying body
74 longitudinal ultrasonic transducer
76 first end
78 second end
80 coupling seat
82 proximal portion
84 distal portion
86 threaded connection
88 seat cavity
90 control means
92 asymmetrical portion
94 inclined section
a angle of incidence
λ wavelength
d diameter of the stem
d' the diameter of the waveguide
D incident direction defining an incident axis
L length
S element plane
P oscillation plane
X tertiary direction defining a tertiary axis
Y secondary direction defining a secondary axis
Z prevailing development direction defining a prevailing development axis
Z1 development direction of the waveguide means defining an axis of waveguide means
Z' assembly direction

The invention claimed is:

1. An ultrasonic system comprising:
generator means of ultrasonic microvibrations;
waveguide means connected to and extending away from the generator means to bend at least in part; and
an operating element joined to a stationary bending node of the waveguide means, so that flexural microvibrations are transmitted by the waveguide means to the operating element as alternate torsional or flexural microvibrations, wherein
said generator means comprise at least one ultrasonic transducer coaxially arranged to a prevailing development direction of the waveguide means;
a distal portion of said waveguide means extends along a direction of development of the waveguide means defining an axis of waveguide means (Z or D);
said operating element extends along a direction defining a secondary or tertiary axis (Y or X); wherein
said axis of waveguide means (Z or D) and said secondary or tertiary axis (Y or X) are substantially orthogonal and incident to each other and define an oscillation plane (P);
and wherein
axes (Y or X, Z, D) of the operating element, generator means and waveguide means are coplanar.

2. The ultrasonic system according to claim 1, wherein the generator means are configured to bend the waveguide means in the oscillation plane (P), by means of stationary ultrasonic microvibrations; and/or wherein
said axis of waveguide means (Z or D) and said secondary or tertiary axis (Y or X) are orthogonal to each other and incident in said stationary bending node of the waveguide means.

3. The ultrasonic system according to claim 2, wherein the operating element develops outside the oscillation plane (P) so that the flexural microvibrations are transmitted as torsional microvibrations within said operating element; and/or wherein
said waveguide means at least partly bend in the oscillation plane (P); and wherein said axis of waveguide means (Z or D) and said secondary axis (Y) are orthogonal and incident to each other and define a single plane (S) orthogonal to said oscillation plane (P).

4. The ultrasonic system according to claim 2, wherein the operating element develops in a substantially parallel, or coincident, plane with respect to the oscillation plane (P) so that the flexural microvibrations are transmitted as flexural microvibrations within said operating element; and/or wherein
said waveguide means at least partly bend in the oscillation plane (P); and wherein
said axis of waveguide means (Z or D) and said tertiary axis (X) are orthogonal and incident to each other and define a single plane (S) coincident with said oscillation plane (P).

5. The ultrasonic system according to claim 1, wherein the generator means and the waveguide means are received in a substantially complete manner in the oscillation plane (P), and are aligned along a prevailing development direction of the waveguide means; and/or wherein
said waveguide means or a waveguide body thereof comprise an inclined section which extends along an incident direction with respect to the prevailing development direction, with a predetermined angle of incidence (a); and/or wherein
said predetermined angle of incidence is between 5 DEG and 45 DEG, or wherein
said inclined section engages in said waveguide means, or waveguide body, at a point corresponding to the stationary bending node of the waveguide means or waveguide body.

6. The ultrasonic system according to claim 5, wherein one or more coupling seats comprise a seat cavity which extends towards inside of the waveguide body, in which complementary coupling threads are arranged.

7. The ultrasonic system according to claim 1, wherein the generator means are configured to generate longitudinal microvibrations, transmitted along the waveguide means in the prevailing development direction; and/or wherein
the generator means comprise at least two piezoelectric elements mutually rotated by 90° around the prevailing direction/development axis (Z), and wherein connection of the operating element to the waveguide means takes place in the stationary bending node and wherein between the development axis of the generator means, or waveguide means, and the development axis of the operating element, orthogonality is provided.

8. The ultrasonic system according to claim 7, wherein the waveguide means distally comprise an element-carrying body connected to the operating element and at least one guide loop, which develops radially with respect to said prevailing development direction, configured to transform the longitudinal microvibrations into torsional microvibrations to the operating element.

9. The ultrasonic system according to claim 8, wherein the operating element is rigidly joined to the waveguide means or to the element-carrying body of the waveguide means, at the stationary bending node.

10. The ultrasonic system according to claim 8, wherein the operating element is a piece separated from the waveguide means or the element-carrying body of the waveguide means; and/or wherein
the operating element is joined to the waveguide means or the element-carrying body of the waveguide means in a removable manner in said stationary bending node of the waveguide means.

11. The ultrasonic system according to claim 8, wherein the operating element is connected to the waveguide means, or to the element-carrying body of said waveguide means, through at least one transmission body integrated in or applied to the operating element, said at least one transmission body being configured and/or tuned to amplify or dampen the microvibrations received from the generator means.

12. The ultrasonic system according to claim 11, wherein the operating element develops, or the operating element and the at least one transmission body develop, away from the waveguide means by a length (L) comprised in a neighborhood (I) of a quarter, or a multiple integer (n) thereof, of a wavelength ($\lambda$) of the torsional or flexural microvibrations generated in the operating element, said neighborhood (I) being less than or equal to $\lambda/10$; and/or wherein
the operating element develops, or the operating element and the at least one transmission body develop, away from the waveguide means by a length (L) comprised in a neighborhood (I) of a quarter, or a multiple integer (n) thereof, of the wavelength ($\lambda$) of the torsional or flexural microvibrations generated in the operating element, said neighborhood (I) being less than or equal to $\lambda/40$.

13. The ultrasonic system according to claim 1, wherein the operating element extends along a secondary axis (Y) incident or substantially orthogonal with respect to the oscillation plane (P), said secondary axis (Y) forming a symmetry axis of said operating element.

14. The ultrasonic system according claim 1, wherein the operating element develops at least partly along the tertiary axis (X) substantially parallel to, and optionally received in, the oscillation plane (P), wherein said tertiary axis (X) forms a symmetry axis of said operating element.

15. The ultrasonic system according to claim 1, wherein the operating element comprises a helical stem which develops helically along the secondary axis (Y), so that a distal portion of the operating element is susceptible to oscillate in percussion, with a longitudinal motion component, in addition to torsional oscillation, alternating along said secondary axis (Y).

16. The ultrasonic system according to claim 1, wherein the generator means comprise at least one ultrasonic transducer comprising piezoelectric elements placed in electrical contact with at least one pair of contact electrodes, each piezoelectric element comprising a pair of half-elements with mutually opposite polarization directions and placed side by side in the oscillation plane (P), so that, upon application of an alternating electrical voltage to the at least one pair of contact electrodes alternatively a half-element expands while the other half-element of the pair contracts to generate the flexural microvibrations in the generator means and in the waveguide means.

17. The ultrasonic system according to claim 1, wherein a distal end of the waveguide means defines one or more radial coupling seats for connection of the operating element; or wherein
the waveguide means delimit two radial coupling seats oriented so that the tertiary axis (X) of the operating element in a coupling seat is incident or substantially orthogonal with respect to the secondary axis (Y) of an operating element engaged in the other coupling seat; and/or wherein
each coupling seat is configured for releasable connection of an independent operating element to the ultrasonic system.

18. The ultrasonic system according to claim 1, wherein the operating element comprises a drilling bit, a material removal cutter, a (semi-)spherical element, a reamer member or a cutting member.

19. The ultrasonic system according to claim 1, wherein the ultrasonic system is a surgical instrument, including a bone drill, or a dental instrument.

20. The ultrasonic system according to claim 19, further comprising control means of the generator means, configured to control a frequency of the ultrasonic microvibrations of said generator means to values such that the microvibrations of the operating element are in a frequency range of 20-60 KHz to selectively remove at least part of mineralized structures, including teeth or bones, preserving integrity of lower density tissues, including soft tissues.

21. A device for oral and/or dental and/or bone surgery comprising an ultrasonic system according to claim 1.

* * * * *

UNITED STATES PATENT AND TRADEMARK OFFICE
CERTIFICATE OF CORRECTION

| | | |
|---|---|---|
| PATENT NO. | : 11,864,777 B2 | Page 1 of 1 |
| APPLICATION NO. | : 17/050516 | |
| DATED | : January 9, 2024 | |
| INVENTOR(S) | : Niccolò Cerisola and Andrea Cardoni | |

It is certified that error appears in the above-identified patent and that said Letters Patent is hereby corrected as shown below:

In the Claims

In Column 21; Line 26, under Claim 5:
Delete "(a)" and insert --($\alpha$)-- in its place Signed and Sealed this
Twentieth Day of February, 2024

*Katherine Kelly Vidal*

Katherine Kelly Vidal
*Director of the United States Patent and Trademark Office*